US009833216B2

(12) United States Patent
Ohuchi et al.

(10) Patent No.: US 9,833,216 B2
(45) Date of Patent: Dec. 5, 2017

(54) ULTRASONIC DIAGNOSIS APPARATUS AND IMAGE PROCESSING METHOD

(71) Applicant: Toshiba Medical Systems Corporation, Otawara-shi (JP)

(72) Inventors: Hiroyuki Ohuchi, Otawara (JP); Takuya Sasaki, Nasu (JP); Yoshitaka Mine, Nasushiobara (JP); Tokiko Mitobe, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 443 days.

(21) Appl. No.: 14/566,446

(22) Filed: Dec. 10, 2014

(65) Prior Publication Data

US 2015/0094569 A1    Apr. 2, 2015

Related U.S. Application Data

(63) Continuation of application No. PCT/JP2013/067282, filed on Jun. 24, 2013.

(30) Foreign Application Priority Data

Jun. 25, 2012   (JP) .................................. 2012-142340
Jun. 24, 2013   (JO) .................................. 2013-131950

(51) Int. Cl.
*A61B 8/08*     (2006.01)
*A61B 8/00*     (2006.01)
*A61B 8/14*     (2006.01)

(52) U.S. Cl.
CPC ............ *A61B 8/0841* (2013.01); *A61B 8/145* (2013.01); *A61B 8/4444* (2013.01); *A61B 8/463* (2013.01);
(Continued)

(58) Field of Classification Search
CPC ..... A61B 8/0841; A61B 8/145; A61B 8/4444; A61B 8/4488; A61B 8/4494; A61B 8/461;
(Continued)

(56) References Cited

U.S. PATENT DOCUMENTS

2007/0016035 A1    1/2007    Hashimoto
2011/0249878 A1   10/2011   Pagoulatos et al.
2012/0253181 A1   10/2012   Okamura et al.

FOREIGN PATENT DOCUMENTS

JP      9-122067 A     5/1997
JP    2000-166918 A    6/2000
(Continued)

OTHER PUBLICATIONS

Office Action issued Nov. 8, 2016 in Japanese Patent Application No. 2013-131950.
(Continued)

*Primary Examiner* — Michael Rozanski
(74) *Attorney, Agent, or Firm* — Oblon, McClelland, Maier & Neustadt, L.L.P.

(57) ABSTRACT

An ultrasonic diagnosis apparatus according to an embodiment includes a scan controller, an image generator, a detector, an image generation controller, an image combiner and a display controller. The scan controller causes to execute a first scan for performing ultrasound transmission in a first direction and a second scan for performing ultrasound transmission in each of a plurality of directions. The image generator generates first ultrasonic image data through the first scan and generates a second ultrasonic image data group through the second scan. The detector detects a line segment based on the second ultrasonic image data group. The image generation controller controls to generate needle image data based on information about the line segment. The image combiner generates composite image data of the first ultrasonic image data and the needle image data. The display controller controls the composite image data to be displayed.

13 Claims, 13 Drawing Sheets

(52) U.S. Cl.
CPC .......... *A61B 8/5207* (2013.01); *A61B 8/5223* (2013.01); *A61B 8/5246* (2013.01); *A61B 8/4488* (2013.01); *A61B 8/4494* (2013.01); *A61B 8/461* (2013.01); *A61B 8/54* (2013.01)

(58) Field of Classification Search
CPC ..... A61B 8/463; A61B 8/5207; A61B 8/5223; A61B 8/5246; A61B 8/54
See application file for complete search history.

(56) References Cited

FOREIGN PATENT DOCUMENTS

| | | |
|---|---|---|
| JP | 2004-208859 A | 7/2004 |
| JP | 2006-320378 A | 11/2006 |
| JP | 2007-301122 A | 11/2007 |
| JP | 2008-012150 A | 1/2008 |
| JP | 2012-213606 A | 11/2012 |

OTHER PUBLICATIONS

International Search Report dated Sep. 10, 2013 for PCT/JP2013/067282 filed Jun. 24, 2013 with English Translation.
International Written Opinion dated Sep. 10, 2013 for PCT/JP2013/067282 filed Jun. 24, 2013.

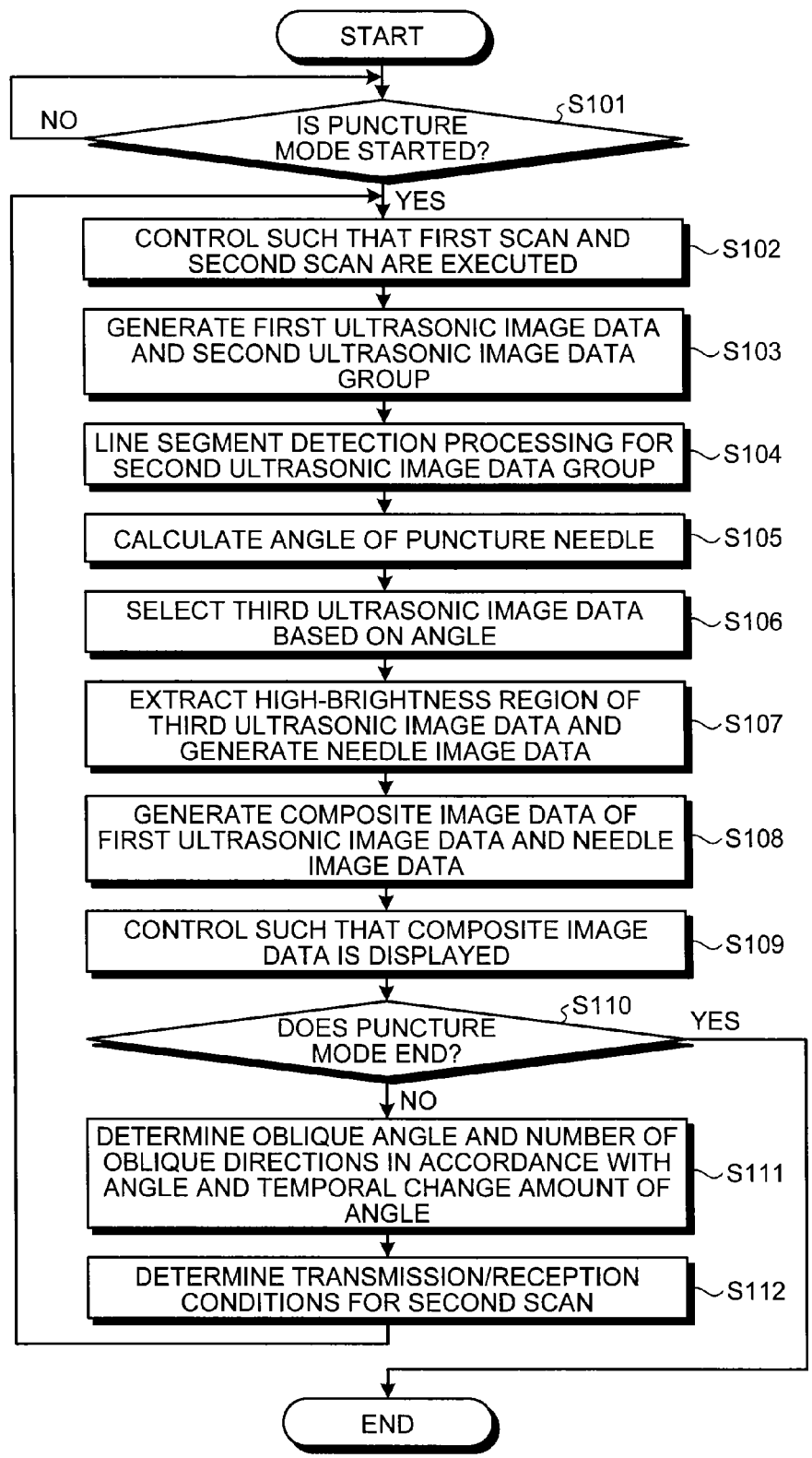

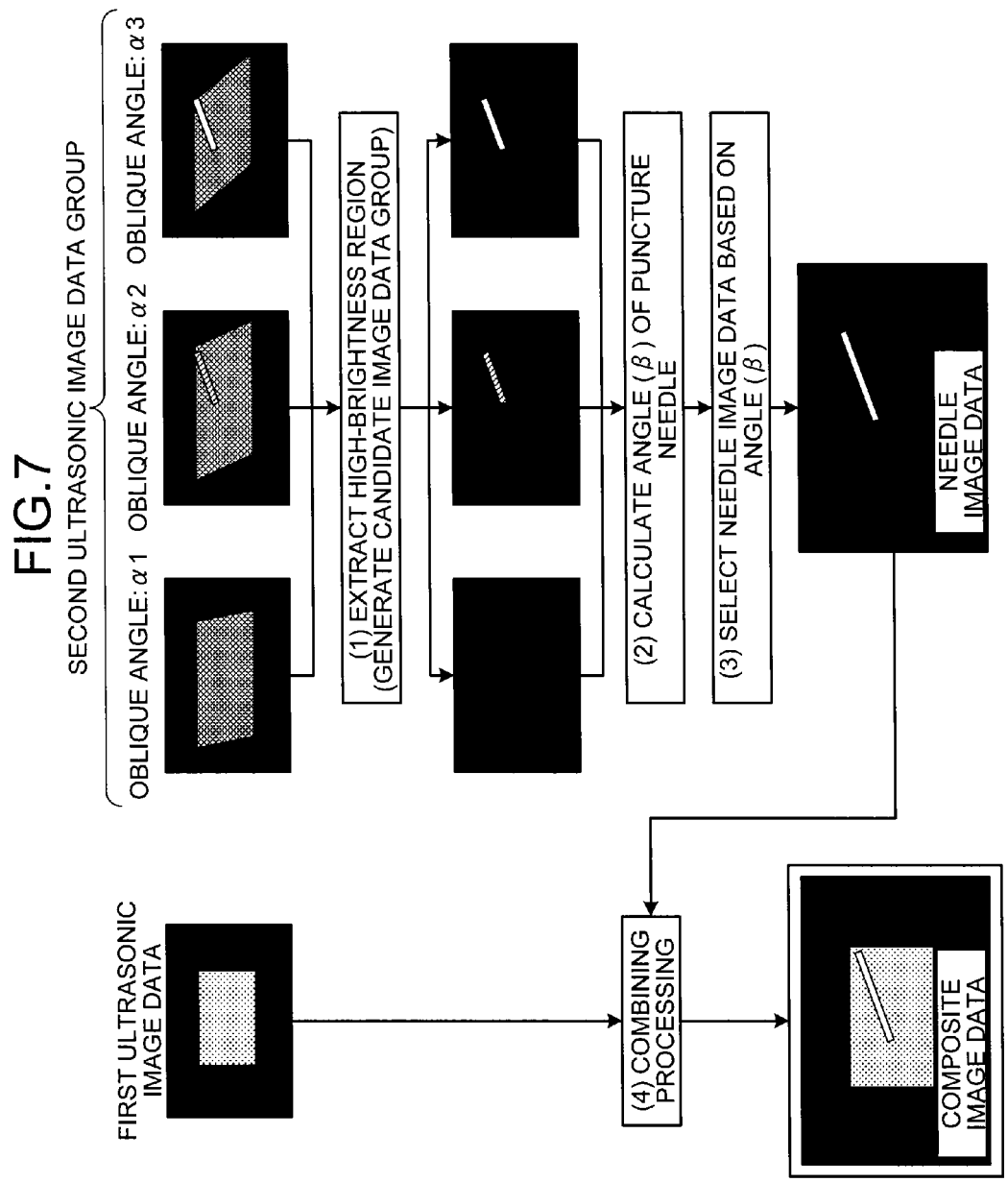

ULTRASONIC DIAGNOSIS APPARATUS AND IMAGE PROCESSING METHOD

CROSS-REFERENCE TO RELATED APPLICATIONS

This application is a continuation of PCT international application Ser. No. PCT/JP2013/067282 filed on Jun. 24, 2013 which designates the United States, incorporated herein by reference, and which claims the benefit of priority from Japanese Patent Application No. 2012-142340, filed on Jun. 25, 2012, and Japanese Patent Application No. 2013-131950, filed on Jun. 24, 2013, the entire contents of which are incorporated herein by reference.

FIELD

Embodiments described herein relate generally to an ultrasonic diagnosis apparatus and an image processing method.

BACKGROUND

Ultrasonic diagnosis apparatuses have been frequently used when puncture using a puncture needle such as biopsy and radio frequency ablation (RFA) is performed, because they can display an ultrasonic image immediately below an ultrasound probe in real-time. If puncture is performed with a puncture guide attached to an ultrasound probe, the angle at which the puncture needle is inserted is limited. Puncture is therefore often performed freehand without using a puncture guide, based on the positional relationship between a lesion and a blood vessel. However, the puncture needle is sometimes obscured due to the effects of the position of a lesion or the introduction angle of the puncture needle. In such a case, puncture is performed by looking at the motion of tissues when the puncture needle is moved.

In recent years, a technique of generating an ultrasonic image (needle image) in which a puncture needle is imaged with high brightness has been known. In this technique, an oblique scan is performed by applying an ultrasonic beam perpendicular to a puncture needle in order to improve the visibility of the puncture needle during puncture. A technique of generating and displaying a composite image of a needle image and a living body image is also known, in which, in addition to generation of a needle image, an ultrasonic image (living body image) in which a living tissue is imaged is generated by performing a normal ultrasound scan without performing an oblique scan.

Objects whose brightness is increased by an oblique scan include not only a puncture needle but also a living tissue perpendicular to the transmission direction of ultrasound. When an oblique scan is performed, grating lobes are produced due to the beam shape and artifacts are produced in the image. Furthermore, the brightness of the puncture needle decreases as the puncture needle is displaced from immediately below the ultrasound probe. In particular when puncture is performed freehand, the angle of the puncture needle is not always constant.

BRIEF DESCRIPTION OF THE DRAWINGS

FIG. 6 is a flowchart for explaining an example of a processing by the ultrasonic diagnosis apparatus according to the first embodiment;

FIG. 7 is a diagram illustrating an overview of an image generation control processing performed in a second embodiment;

DETAILED DESCRIPTION

An ultrasonic diagnosis apparatus according to an embodiment includes a scan controller, an image generator, a detector, an image generation controller, an image combiner and a display controller. The scan controller causes an ultrasound probe to execute a first scan for performing ultrasound transmission in a first direction relative to a transducer element surface for the purpose of visualizing a tissue of a subject and a second scan for performing ultrasound transmission in each of a plurality of directions relative to the transducer element surface, in ultrasound scanning of the subject into which a puncture needle is inserted. The image generator generates first ultrasonic image data using a reflected wave received by the ultrasound probe through the first scan and generates a second ultrasonic image data group comprising ultrasonic image data for each of the plurality of the directions using a reflected wave received by the ultrasound probe through the second scan. The detector detects a line segment based on the second ultrasonic image data group. The image generation controller controls the image generator to generate needle image data in which the puncture needle is imaged, based on information about the line segment detected by the detector. The image combiner generates composite image data of the first ultrasonic image data and the needle image data. The display controller controls the composite image data to be displayed on a predetermined display.

Embodiments of an ultrasonic diagnosis apparatus will be described in details below with reference to the accompanying drawings.

First Embodiment

Figure 1:
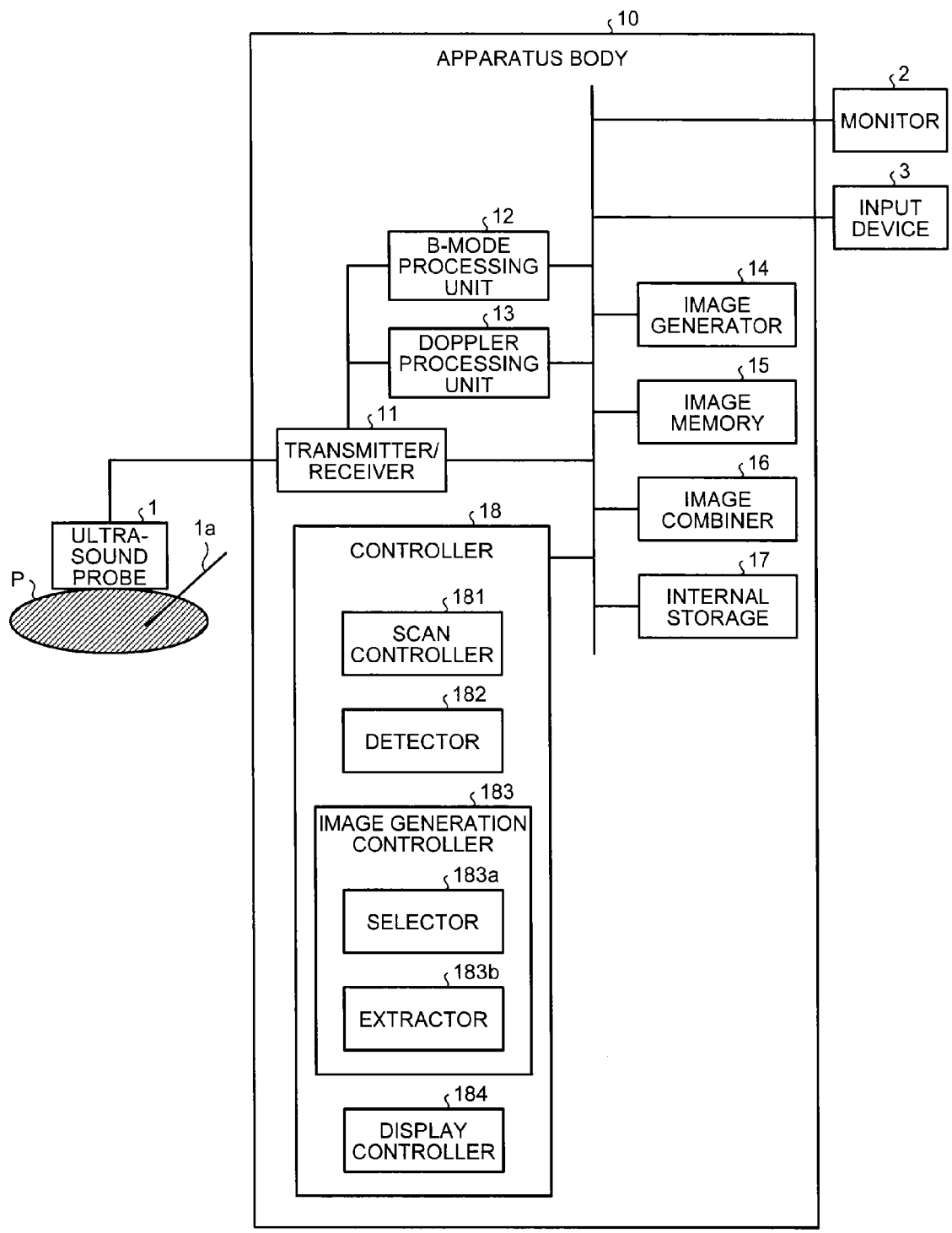
FIG. 1 is a diagram illustrating an exemplary configuration of an ultrasonic diagnosis apparatus according to a first embodiment.

First of all, a configuration of an ultrasonic diagnosis apparatus according to a first embodiment will be described. FIG. 1 is a diagram illustrating an exemplary configuration of the ultrasonic diagnosis apparatus according to the first embodiment. As illustrated in FIG. 1, the ultrasonic diagnosis apparatus according to the first embodiment has an ultrasound probe 1, a monitor 2, an input device 3, and an apparatus body 10.

The ultrasound probe 1 is removably connected to the apparatus body 10. The ultrasound probe 1 includes a plurality of piezoelectric transducer elements. The plurality of the piezoelectric transducer elements generate ultrasonic waves based on a drive signal supplied from a transmitter/receiver 11 of the apparatus body 10 described later. The ultrasound probe 1 receives a reflected wave from a subject P and converts the reflected wave into an electrical signal. The ultrasound probe 1 additionally has a matching layer provided for the piezoelectric transducer elements and a backing material for preventing propagation of an ultrasonic wave backward from the piezoelectric transducer elements.

When an ultrasonic wave is transmitted from the ultrasound probe 1 to the subject P, the transmitted ultrasonic wave is successively reflected on a surface of discontinuity of acoustic impedance in tissues inside the body of the subject P and is received as an echo signal by the piezoelectric transducer elements of the ultrasound probe 1. The amplitude of the received echo signal depends on the difference in acoustic impedance on the surface of discontinuity on which the ultrasonic wave is reflected. In a case where the transmitted ultrasonic pulse is reflected on a moving blood flow or a surface such as a heart wall, the echo signal undergoes a frequency shift depending on the velocity component of the moving target relative to the ultrasound transmission direction, due to the Doppler effect.

It is noted that the first embodiment is applicable in either case where the ultrasound probe 1 illustrated in FIG. 1 is a one-dimensional ultrasound probe having a plurality of piezoelectric transducer elements arranged in line, a one-dimensional ultrasound probe in which a plurality of piezoelectric transducer elements arranged in line are mechanically swung, or a two-dimensional ultrasound probe in which a plurality of piezoelectric transducer elements are arranged in a two-dimensional array.

In the first embodiment, in order to perform biopsy or radio frequency ablation, a doctor who refers to the ultrasonic image data displayed on the monitor 2 through ultrasound transmission/reception performed by the ultrasound probe 1 inserts a puncture needle 1a to a target site of the subject P from the proximity of the body surface in abutment with the ultrasound probe 1. In the first embodiment, puncture with the puncture needle 1a is performed freehand. However, the first embodiment is also applicable in a case where puncture is performed with the puncture needle 1a attached to a puncture adapter mounted on the ultrasound probe 1.

The input device 3 includes, for example, a mouse, a keyboard, a button, a panel switch, a touch command screen, a foot switch, and a trackball for accepting a variety of setting requests from the operator of the ultrasonic diagnosis apparatus and transferring the accepted setting requests to the apparatus body 10. For example, when the operator presses a stop button or a freeze button of the input device 3, transmission/reception of an ultrasonic wave is terminated to cause the ultrasonic diagnosis apparatus according to the first embodiment to pause. The operator can also make an initial setting of the oblique angle of ultrasound transmission for performing a second scan (oblique scan) described later through the input device 3.

The monitor 2 displays graphical user interfaces (GUIs) for the operator of the ultrasonic diagnosis apparatus to input a variety of setting requests using the input device 3 or displays an ultrasonic image generated in the apparatus body 10.

The apparatus body 10 is an apparatus for generating ultrasonic image data based on the reflected wave received by the ultrasound probe 1. The apparatus body 10 has the transmitter/receiver 11, a B-mode processing unit 12, a Doppler processing unit 13, an image generator 14, an image memory 15, an image combiner 16, an internal storage 17, and a controller 18, as illustrated in FIG. 1.

The transmitter/receiver 11 includes a trigger generating circuit, a delay circuit, a pulser circuit, and the like for supplying a drive signal to the ultrasound probe 1. The pulser circuit repeatedly generates a rate pulse for forming a transmission ultrasonic wave at a predetermined rate frequency. The delay circuit provides each rate pulse generated by the pulser circuit with a delay time for each piezoelectric transducer element that is required to focus ultrasonic waves generated from the ultrasound probe 1 into a beam and decide transmission directivity. The trigger generating circuit applies a drive signal (driving pulse) to the ultrasound probe 1 at a timing based on the rate pulse. In other words, the delay circuit adjusts the transmission direction from the piezoelectric transducer element surface as desired by changing the delay time provided to each rate pulse.

The driving pulse is transmitted from the pulse circuit to the piezoelectric transducer element in the ultrasound probe 1 through a cable and is then converted from an electrical signal to mechanical vibration in the piezoelectric transducer element. The mechanical vibration is transmitted as an ultrasonic wave in the inside of a living body. Here, ultrasonic waves with transmission delay time varying among the piezoelectric transducer elements are focused and propagate in a predetermined direction. That is, the delay circuit adjusts the transmission direction from the piezoelectric transducer element surface as desired by changing the transmission delay time provided to each rate pulse.

The transmitter/receiver 11 has a function of capable of instantaneously changing a transmission frequency, a transmission driving voltage, and the like for executing a predetermined scan sequence, based on an instruction of the controller 18 described later. In particular, the transmission driving voltage is changed by a linear amplifier-type transmission circuit capable of instantaneously switching its values or by a mechanism for electrically switching a plurality of power supply units.

In addition, the transmitter/receiver 11 includes an amplifier circuit, an A/D converter, an adder, and the like for performing a variety of processing on the echo signal received by the ultrasound probe 1 to generate echo data. The amplifier circuit performs a gain correction processing by amplifying the echo signal for each channel. The A/D converter A/D-converts the echo signal having the gain corrected and provides a delay time required to determine the reception directivity. The adder performs an addition processing for the echo signal based on the provided delay time to generate echo data. The addition processing by the adder enhances the echo component from the direction corresponding to the reception directivity of the echo signal.

As described above, the transmitter/receiver 11 controls the transmission directivity and the reception directivity in transmission/reception of an ultrasonic wave. The transmitter/receiver 11 has a function of instantaneously changing delay information, a transmission frequency, a transmission driving voltage, the number of elements in the aperture, and the like, under the control of the controller 18 described later. The transmitter/receiver 11 can also transmit and receive a waveform different for each frame or rate.

The B-mode processing unit 12 receives echo data from the transmitter/receiver 11 and performs logarithmic amplification, envelop detection, and the like on the received echo data to generate data (B-mode data) in which a signal intensity is represented with the luminance of brightness.

The Doppler processing unit 13 receives echo data from the transmitter/receiver 11, frequency-analyzes the velocity information from the received echo data, extracts blood flow, tissue, or contrast medium echo components due to the Doppler effect, and generates data (Doppler data) in which moving target information such as average velocity, distribution, and power is extracted at multiple points. The data generated by the B-mode processing unit 12 and the Doppler processing unit 13 is also called raw data.

The B-mode processing unit 12 can change the frequency range to be visualized, by changing the detection frequency. Using this function of the B-mode processing unit 12, contrast harmonic imaging (CHI) can be executed. Specifically, the B-mode processing unit 12 can separate echo data (harmonic data or subharmonic data) in which contrast medium (micro-bubbles foam or bubbles) is the source of reflection and echo data (fundamental data) in which tissues in the subject P are a source of reflection, from the echo data of the subject P into which the contrast medium is injected. The B-mode processing unit 12 can generate B-mode data for generating contrast image data.

In addition, this function of the B-mode processing unit 12 can be used to generate B-mode data for generating tissue image data having noise components removed therefrom, by separating harmonic data or subharmonic data from the echo data of the subject P in tissue harmonic imaging (THI). The B-mode processing unit 12 can also generate B-mode data for generating contrast image data and B-mode data for generating tissue image data by a signal processing method based on phase modulation (PM), amplitude modulation (AM), or amplitude modulation-phase modulation (AMPM) in CHI and THI.

The image generator 14 generates ultrasonic image data from data generated by the B-mode processing unit 12 and the Doppler processing unit 13. Specifically, the image generator 14 generates B-mode image data that represents the intensity of reflected wave by brightness from the B-mode data generated by the B-mode processing unit 12. The image generator 14 also generates color Doppler image data as average velocity image data, distribution image data, power image data, or an image including a combination thereof that represents moving target information from the Doppler data generated by the Doppler processing unit 13.

Here, the image generator 14 scan-converts a scan line signal train in ultrasound scanning into a scan line signal train in a video format typically of television and generates ultrasonic image data as a display image. The image generator 14 performs, as a variety of image processing in addition to scan-conversion, for example, image processing of regenerating a mean value image of brightness (smoothing processing) or image processing using a differential filter in an image (edge enhancement processing), by using a plurality of image frames after scan-conversion.

The image generator 14 is installed with a storage memory for storing image data and can perform, for example, a re-construction processing for three-dimensional images. The operator can invoke images recorded during a test from the storage memory installed in the image generator 14, for example, after diagnosis.

The image combiner 16 combines character information of various parameters, such as a scale, a body mark, etc., with the ultrasonic image generated by the image generator 14 and outputs the combined image as a video signal to the monitor 2. The image combiner 16 also generates composite image data in which a plurality of images are superimposed on one another. The composite image data generated by the image combiner 16 according to the first embodiment will be detailed later.

The image memory 15 is a memory for storing therein the ultrasonic image data generated by the image generator 14 and the composite image data combined by the image combiner 16. For example, the image memory 15 stores therein ultrasonic images corresponding to a plurality of frames immediately before a FREEZE button is pressed. The ultrasonic diagnosis apparatus can display ultrasonic moving images by successively displaying images stored in the image memory 15 (cine-display).

The internal storage 17 stores therein a control program for performing ultrasound transmission/reception, image processing, and display processing, diagnosis information (for example, a patient ID, the doctor's observation, etc.), and various data such as diagnosis protocols and a variety of body marks. The internal storage 17 is also used to retain image data stored in the image memory 15, as necessary. The data stored in the internal storage 17 may be transferred to an external peripheral device via a not-shown interface circuits.

The controller 18 controls the entire processing in the ultrasonic diagnosis apparatus. Specifically, the controller 18 controls the processing in the transmitter/receiver 11, the B-mode processing unit 12, the Doppler processing unit 13, the image generator 14, and the image combiner 16, based on a variety of setting requests input through the input device 3 by the operator and a variety of control programs and data read from the internal storage 17. For example, a scan controller 181 illustrated in FIG. 1 controls an ultrasound scan by the ultrasound probe 1 through the transmitter/receiver 11. A display controller 184 illustrated in FIG. 1 controls ultrasonic image data or composite image data store in the image memory 15 to be displayed on the monitor 2.

The controller 18 according to the first embodiment includes, in addition to the scan controller 181 and the display controller 184, a detector 182 and an image generation controller 183 as illustrated in FIG. 1. The image generation controller 183 includes a selector 183a and an extractor 183b as illustrated in FIG. 1.

The processing executed by the scan controller 181, the detector 182, the selector 183a, the extractor 183b, and the display controller 184 in the first embodiment will be detailed later.

The overall configuration of the ultrasonic diagnosis apparatus according to the first embodiment has been described above. Based on such a configuration, the ultrasonic diagnosis apparatus according to the first embodiment generates ultrasonic image data by capturing an image of a living tissue of the subject P into which the puncture needle 1a is inserted. The ultrasonic diagnosis apparatus according to the first embodiment generates composite image data in which the visibility of the puncture needle 1a is improved irrespective of the angle of the puncture needle 1a, through the control processing by the controller 18 as described in details below.

For example, when the operator presses a puncture mode start button of the input device 3, the ultrasonic diagnosis apparatus according to the first embodiment starts the processing described below. For example, when the operator presses a puncture mode end button of the input device 3, the ultrasonic diagnosis apparatus according to the first embodiment terminates the processing described below.

First, the scan controller 181 causes the ultrasound probe 1 to execute a first scan and a second scan in ultrasound scanning of a subject P into which the puncture needle 1a is inserted.

The first scan is a scan in which ultrasound transmission is performed in a first direction relative to the transducer element surface for the purpose of visualizing a tissue of the subject P. Specifically, the first scan is an ultrasound scan in which ultrasound transmission in the first direction that is most suitable for visualizing a living tissue of the subject P is performed along the direction of arrangement of the transducer elements. Specifically, the first direction is a direction perpendicular to the transducer element surface of the ultrasound probe 1. For example, the first direction is a direction perpendicular to the lateral direction. The first direction may be a direction other than the direction perpendicular to the transducer element surface if it is an ultrasound transmission direction that is most suitable for visualizing a tissue of the subject P.

Here, as the ultrasound transmission/reception conditions set in the first scan, the conditions for the THI mode described above are set in order to obtain image data in which a living tissue is well imaged. However, for example, the conditions for the normal B-mode may be set as long as image data in which a living tissue is well imaged is obtained.

The second scan is a scan in which ultrasound transmission is performed in each of a plurality of directions relative to the transducer element surface. Specifically, the second scan is an ultrasound scan (oblique scan) in which ultrasound transmission is performed in each of a plurality of directions for the purpose of searching for an ultrasound transmission direction that is most suitable for visualizing the puncture needle 1a inserted into the subject P. In the second scan, ultrasound transmission is performed along the direction of arrangement of the transducer elements in each of a plurality of directions. In the first embodiment, each direction of a plurality of directions described above is a direction other than the direction perpendicular to the transducer element surface of the ultrasound probe 1. For example, each direction of a plurality of directions is a direction other than the direction perpendicular to the lateral direction.

Here, the ultrasound transmission/reception conditions for the second scan may be the same as in the first scan but, desirably, are set such that artifacts due to grating lobes are minimized and a received signal from the puncture needle 1a is larger. In the second scan, therefore, for example, the ultrasound transmission/reception conditions are set such that a transmission waveform at a relatively low frequency is transmitted from the ultrasound probe 1 and the fundamental component of the transmitted ultrasonic wave is used in the processing of the received signal.

Figure 2:
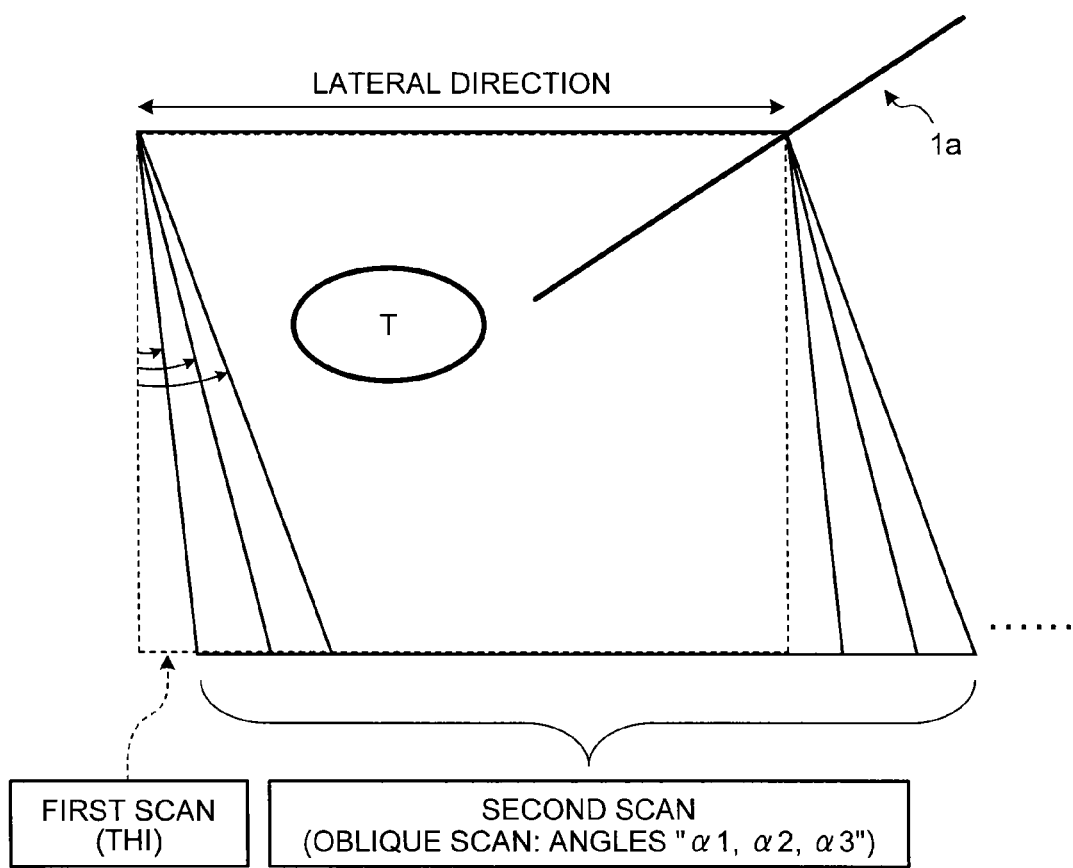
FIG. 2 is a diagram for explaining a scan controller according to the first embodiment.

FIG. 2 is a diagram for explaining the scan controller according to the first embodiment. In an example illustrated in FIG. 2, the puncture needle 1a is inserted toward a target site (T). In this state, the scan controller 181 allows execution of ultrasound transmission in a direction perpendicular to the lateral direction as the first scan, as illustrated in FIG. 2, in the same manner as the scan performed to generate B-mode image data or THI image data. The scan controller 181 allows execution of an oblique scan, for example, at three different angles "α1, α2, α3" as the second scan, as illustrated in FIG. 2. The value or number of the oblique angles may be initially set or may be set by the operator before puncture.

The image generator 14 illustrated in FIG. 1 generates first ultrasonic image data using a reflected wave received by the ultrasound probe 1 in the first scan. In the present embodiment, the first ultrasonic image data is THI image data using a harmonic component. In addition, the image generator 14 generates a second ultrasonic image data group that consists of ultrasonic image data for each of a plurality of directions using a reflected wave received by the ultrasound probe 1 in the second scan. The second ultrasonic image data group includes a plurality of ultrasonic image data with different oblique angles.

In the example above, the image generator 14 generates ultrasonic image data with "the oblique angle: α1", ultrasonic image data with "the oblique angle: α2", and ultrasonic image data with "the oblique angle: α3" as the second ultrasonic image data group. In the following, the ultrasonic image data generated through the second scan is also referred to as oblique image data.

In the first embodiment, an image generation control processing by the image generation controller 183 is performed using the processing result by the detector 182. The detector 182 has a function of detecting a line segment imaged in image data. In the first embodiment, the detector 182 further has a function of calculating the angle of the detected line segment. The detector 182 detects a line segment based on the second ultrasonic image data group. In the first embodiment, the detector 182 further calculates the angle of the detected line segment. The detector 182 calculates the angle of the detected line segment as the angle of the puncture needle 1a. The image generation controller 183 then controls the image generator 14 to generate needle image data in which the puncture needle 1a is imaged, based on information about the line segment detected by the detector 182. The image generation controller 183 according to the first embodiment controls the image generator 14 to generate needle image data in which the puncture needle 1a is imaged, based on the angle calculated by the detector 182. For example, the needle image data is image data in which the puncture needle 1a is imaged with high brightness. In the first embodiment, the detector 182 detects a line segment from the second ultrasonic image data group and calculates the angle of the detected line segment. The image generation controller 183 according to the first embodiment then controls the image generator 14 to generate needle image data in which the puncture needle 1a is imaged with high brightness, based on the angle calculated by the detector 182 for each image data that constitutes the second ultrasonic image data group.

Figure 3:
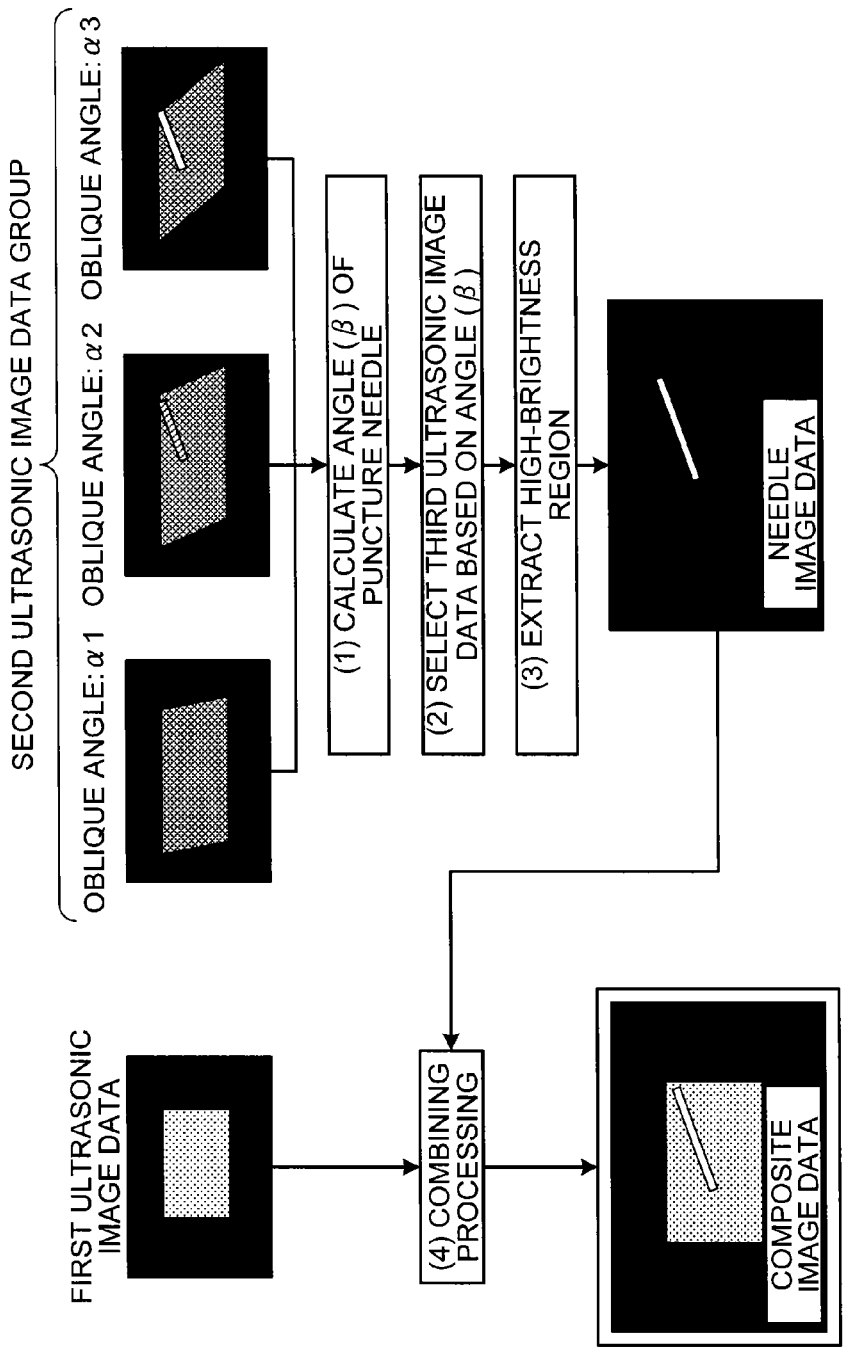
FIG. 3 is a diagram illustrating an overview of an image generation control processing performed in the first embodiment.
Figure 4:
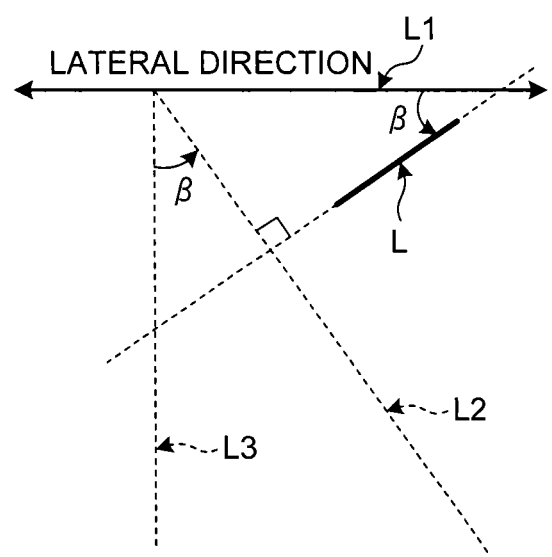
FIG. 4 is a diagram for explaining a detector illustrated in FIG. 1.

An example of the image generation control processing performed in the first embodiment will be described below using FIG. 3 and FIG. 4. FIG. 3 is a diagram illustrating an overview of the image generation control processing performed in the first embodiment. FIG. 4 is a diagram for explaining the detector illustrated in FIG. 1.

As illustrated in FIG. 3, the detector 182 calculates the angle (β) of the puncture needle 1a using 'ultrasonic image data with "the oblique angle: α1", ultrasonic image data with "the oblique angle: α2", and ultrasonic image data with the "oblique angle: α3"' that are the second ultrasonic image data group (see (1) in FIG. 3). For example, the detector 182 performs a line segment detection processing such as Hough transform on the oblique image data.

The detector 182 thus detects a line segment L in the oblique image data, as illustrated in FIG. 4. The detector 182 then calculates the angle (β) formed by "a straight line L1 in the lateral direction (the horizontal direction in image data" and "a straight line including the line segment L", as illustrated in FIG. 4. This angle (β) is the angle also formed by "a straight line L2 perpendicular to the line segment L" and "a straight line L3 perpendicular to the lateral direction" as illustrated in FIG. 4. That is, the angle (β) serves as the oblique angle for performing ultrasound transmission perpendicular to the linear source of reflection corresponding to the line segment L.

Here, it is likely that the linear source of reflection corresponding to the line segment L is the puncture needle 1a. Based on this, the angle (β) serves as the oblique angle for performing ultrasound transmission in the direction perpendicular to the puncture needle 1a. That is, the angle (β) serves as the oblique angle for setting the ultrasound transmission direction most suitable for visualizing the puncture needle 1a. It is noted that the line segment detection processing and the angle calculation processing are not limited to Hough transform, and any method generally known may be used as a method of calculating the angle of a line segment from an image.

Here, the detector 182 calculates a statistical value such as the mean value or median value of angles calculated from image data that constitute the second ultrasonic image data group, as the angle (β). The detector 182 does not perform the angle calculation processing for image data from which no line segment is detected, or image data from which no line segment having a length longer than a predetermined length is detected.

The selector 183a of the image generation controller 183 illustrated in FIG. 1 selects third ultrasonic image data from the second ultrasonic image data group, based on the angle calculated by the detector 182 for each image data that constitutes the second ultrasonic image data group. The third ultrasonic image data is image data generated through ultrasound transmission performed in the direction suitable for visualizing the puncture needle 1a. Specifically, the selector 183a selects image data (third ultrasonic image data) generated through ultrasound transmission performed in a direction at an angle closest to perpendicularity (a right angle) relative to the puncture needle 1a, based on the angle (β) calculated by the detector 182 (see (2) in FIG. 3). More specifically, the selector 183a selects oblique image data with the oblique angle closest to the angle (β) as the third ultrasonic image data. For example, if a plurality of oblique angles set in the second scan are "{α1, α2, α3}={10 degrees, 20 degrees, 30 degrees}" and "β=28 degrees", the selector 183a selects the ultrasonic image data with "the oblique angle: α3=30 degrees" as the third ultrasonic image data.

The extractor 183b of the image generation controller 183 illustrated in FIG. 1 extracts a high-brightness region of the third ultrasonic image data as a puncture needle region (see (3) in FIG. 3). The extractor 183b then controls the image generator 14 to generate needle image data using the extracted puncture needle region.

For example, the extractor 183b searches for a high-brightness region in the vicinity of the line segment detected in the third ultrasonic image data. As an example, the extractor 183b searches for a region having a brightness value equal to or larger than a threshold for high-brightness region extraction among pixels in the vicinity of the line segment detected in the third ultrasonic image data, as a high-brightness region. The image generator 14 then generates needle image data by setting the brightness value of the region excluding the high-brightness region found by the extractor 183b to "0". In this manner, the search for a high-brightness region is restricted to the vicinity of the line segment, whereby needle image data in which only the puncture needle 1a is imaged can be generated by setting the brightness value of a high-brightness region resulting from artifacts or a high-brightness region corresponding to a living tissue with high reflection intensity, to "0".

The image combiner 16 then generates composite image data of the first ultrasonic image data and the needle image data through a combining processing (see (4) in FIG. 3). For example, the image combiner 16 compares the first ultrasonic image data in which a living tissue is well imaged with the brightness value of the needle image data in which the puncture needle 1a is well imaged, pixel by pixel. The image combiner 16 then creates composite image data where the pixel where a brightness value of the needle image data is "0" has the brightness value of the first ultrasonic image data and the pixel where a brightness value of the needle image data is larger than "0" has the brightness value of the needle image data. Image data where only high-brightness needle image data is superimposed on the living tissue image of good image quality can be thus generated. It is noted that the method of generating composite image data is not limited to the brightness value comparison as described above. The composite image data may be generated by simple addition or weighted addition.

The display controller 184 then controls the composite image data to be displayed on the monitor 2. In the present embodiment, the brightness value of the needle image data may be adjusted by performing gain adjustment or dynamic range adjustment before generation of composite image data. As a result of such brightness adjustment, the puncture needle 1a imaged in the needle image data can be highlighted.

Described above is the image generation control processing performed in the first embodiment. In the first embodiment, the scan controller 181 makes a condition change for the second scan, based on the angle calculated by the detector 182.

First, the scan controller 181 changes the direction of ultrasound transmission performed in the second scan, based on the angle calculated by the detector 182. The scan controller 181 also changes the number of directions of ultrasound transmission performed in the second scan, based on the temporal change of the angle calculated by the detector 182. The case where the direction of ultrasound transmission and the number of directions of ultrasound transmission are changed will be described below. In the present embodiment, however, only the direction of ultrasound transmission may be changed, or only the number of directions of ultrasound transmission may be changed.

Figure 5A:
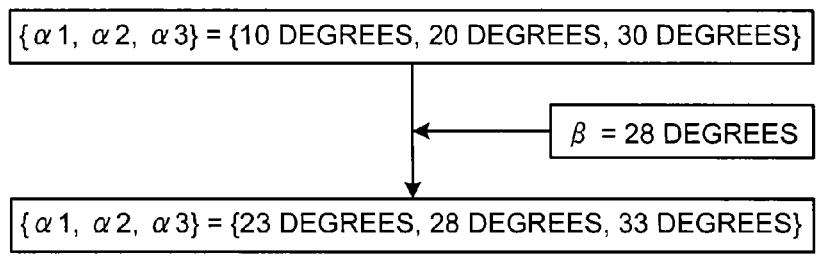
FIG. 5A and FIG. 5B are diagrams illustrating an example of a second scan condition change processing by the scan controller according to the first embodiment.
Figure 5B:
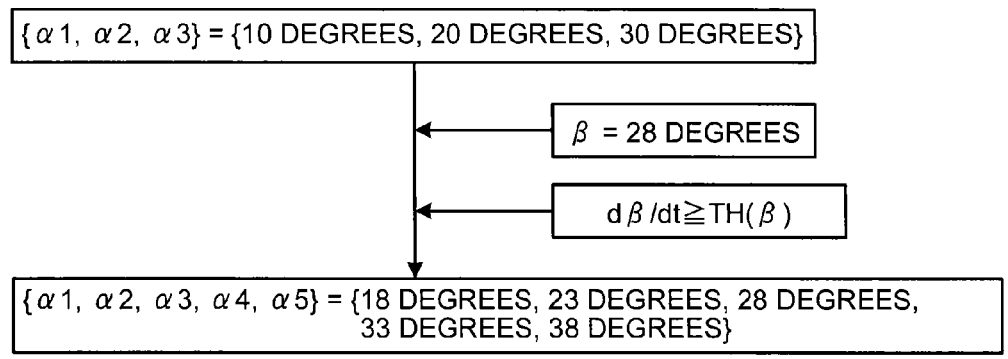

The second scan condition change processing described above will be explained below with reference to FIGS. 5A and 5B. FIG. 5A and FIG. 5B are diagrams illustrating an example of the second scan condition change processing by the scan controller according to the first embodiment.

First, the processing of changing the direction of ultrasound transmission will be described. The scan controller 181 controls such that the oblique angle corresponding to the angle calculated by the detector 182 when one frame of composite image data is generated is included in a plurality of oblique angles in the second scan performed for generating the next frame of composite image data. In addition to this, the scan controller 181 may control such that the interval between a plurality of oblique angles set in the second scan when one frame of composite image data is generated is narrowed in the second scan to be performed for generating the next frame of composite image data.

For example, as illustrated in FIG. 5A, let us consider a case when a plurality of oblique angles set in the second scan when one frame of composite image data is generated are "{α1, α2, α3}={10 degrees, 20 degrees, 30 degrees}" and the angle calculated by the detector 182 is "β=28 degrees".

In this case, the scan controller 181 changes a plurality of oblique angles set in the second scan to be performed for generating the next frame of composite image data to "{α1, α2, α3}={23 degrees, 28 degrees, 33 degrees}", as illustrated in FIG. 5A. In the example illustrated in FIG. 5A, the scan controller 181 changes the second scan performed in three directions at an interval of 10 degrees with "20 degrees" as the center, to the second scan to be performed in three directions including "β=28 degrees" at an interval of 5 degrees with "β=28 degrees" being the center. Accordingly, in the next frame, composite image data in which the puncture needle 1a is depicted more sharply can be generated.

Next, the processing of changing the direction of ultrasound transmission will be described. When puncture is performed freehand, the angle at which the puncture needle 1a is introduced is not always constant and often varies. In some cases, puncture is performed in a situation in which the puncture needle 1a is introduced while avoiding blood vessels. In such a case, the angle at which the puncture needle 1a is introduced varies. The same thing happens when a puncture adapter is used.

Then, for example, the scan controller 181 calculates the temporal change "dβ/dt" of the angle (β) Alternatively, the detector 182 may calculate the temporal change of the angle (β). The scan controller 181 then compares "dβ/dt" with a threshold of the angular change amount "TH(β)", and, if "dβ/dt≥TH(β)", increases the number of directions of ultrasound transmission for the oblique scan.

For example, as illustrated in FIG. 5B, let us consider a case where a plurality of oblique angles set in the second scan when the "n-th" frame of composite image data is generated are "{α1, α2, α3}={10 degrees, 20 degrees, 30 degrees}", and the angle calculated by the detector 182 is "β=28 degrees". It is further assumed that the temporal change (dβ/dt) calculated between the angle obtained when the "(n−1)th" frame of composite image data is generated and the angle obtained when the "n-th" frame of composite image data is generated is "dα/dt≥TH(β)". In this case, the scan controller 181 changes a plurality of oblique angles set in the second scan to be performed for generating the "(n+1)th" frame of composite image data to "{α1, α2, α3, α4, α5}={18 degrees, 23 degrees, 28 degrees, 33 degrees, 38 degrees}" as illustrated in FIG. 5B.

In the example illustrated in FIG. 5B, the scan controller 181 changes the second scan performed in three directions at an interval of 10 degrees with "20 degrees" being the center to the second scan performed in five directions including "β=28 degrees" and being performed at an interval of 5 degrees with "β=28 degrees" being the center. Accordingly, even when the angle of the puncture needle 1a changes a few degrees from the present 28 degrees, the puncture needle 1a is imaged with high brightness in any of the oblique image data in five directions, so that the visibility of the puncture needle 1a in the composite image data can be ensured.

The scan controller 181 changes the ultrasound transmission/reception conditions for the second scan after change, based on the condition change of the second scan. For example, as illustrated in FIG. 5B, when the number of oblique directions is changed from three directions to five directions, the density of transmission/reception beams for generating one frame of oblique image data is set to "⅗" of the present state. The frame rate of the composite image can thus be kept in the present embodiment.

Next, an example of the processing by the ultrasonic diagnosis apparatus according to the first embodiment will be described with reference to FIG. 6. FIG. 6 is a flowchart for explaining an example of the processing by the ultrasonic diagnosis apparatus according to the first embodiment.

As illustrated in FIG. 6, the ultrasonic diagnosis apparatus according to the first embodiment determines whether a puncture mode is started (Step S101). Here, if the puncture mode is not started (No at Step S101), the ultrasonic diagnosis apparatus according to the first embodiment waits until the puncture mode is started.

On the other hand, if the puncture mode is started (Yes at Step S101), the scan controller 181 controls the ultrasound probe 1 to execute the first scan and the second scan are executed (Step S102).

The image generator 14 then generates the first ultrasonic image data and the second ultrasonic image data group (Step S103). The detector 182 then performs a line segment detection processing on the second ultrasonic image data group (Step S104) and calculates the angle of the line segment, that is, the angle of the puncture needle 1a (Step S105).

The selector 183a then selects the third ultrasonic image data based on the angle (Step S106). The extractor 183b extracts a high-brightness region of the third ultrasonic image data. The image generator 14 generates needle image data under the control of the extractor 183b (Step S107).

The image combiner 16 then generates a composite image of the first ultrasonic image data and the needle image data (Step S108). The display controller 184 controls such that the composite image data is displayed (Step S109).

The scan controller 181 then determines whether the puncture mode ends (Step S110). Here, if the puncture mode does not end (No at Step S110), the scan controller 181 determines the oblique angle and the number of oblique directions in accordance with the angle and the temporal change of the angle (Step S111). Specifically, the scan controller 181 determines whether to change the oblique angle and whether to change the number of oblique directions, based on the angle and the temporal change of the angle. The scan controller 181 then determines the oblique angle after change, if the oblique angle is to be changed, and determines the number of oblique directions after change, if the number of oblique directions is to be changed.

The scan controller 181 then determines the transmission/reception conditions for the second scan, based on the result of the decision processing performed at Step S111 (Step S112) and returns to Step S102 to control such that the first scan and the second scan are executed for generating a composite image for the next frame.

On the other hand, if the puncture mode ends (Yes at Step S110), the ultrasonic diagnosis apparatus terminates the processing. The display controller 184 may display the first ultrasonic image data, the third ultrasonic image data, or the second ultrasonic image data group concurrently with the composite image data. In the foregoing description, the puncture mode end determination is performed after display of the composite image at Step S109. In the first embodiment, however, the puncture mode end determination may be performed after the first scan and the second scan are performed at Step S102. That is, the first scan and the second scan may be executed in a sequential order concurrently with the processing at Step S103 to Step S109.

As described above, in the first embodiment, the oblique angle most suitable for visualizing the puncture needle 1a is estimated by detecting a line segment in the oblique image data and calculating the angle of the detected line segment. In the first embodiment, the oblique image data corresponding to the oblique angle closest to the calculated angle is then selected as image data including a region in which the puncture needle 1a is imaged with high brightness. In the first embodiment, the needle image data is then generated by extracting a high-brightness region of the selected oblique image data, and is combined with the first ultrasonic image data.

For example, in order to generate needle image data, it is possible that image data including a region in which the puncture needle 1a is imaged with high brightness is selected from the distribution of brightness values of a plurality of oblique image data with different oblique angles. However, with such a method, it is necessary to apply ultrasonic waves at a plurality of oblique angles in order to image the puncture needle 1a with an unknown puncture angle, with high brightness. Moreover, with such a method, image data in which the puncture needle 1a is imaged with high brightness cannot always be selected, but image data in which the brightness of the puncture needle 1a is low and a bone or artifact is imaged with high brightness may be selected. It is also possible that the position and angle of the puncture needle 1a is detected with a position sensor attached to the puncture needle 1a, and the oblique angle is determined based on the detected angle. However, position sensors are expensive, and it is not practical to attach position sensors to all the puncture needles 1a. It is also possible that a mechanism that allows the operator to set and change the oblique angle is provided to set the oblique angle at which the puncture needle 1a in image data is imaged with high brightness. Such operation, however, is complicated as operation during the puncture procedure and may deteriorate the test efficiency. The operator often wears sterilized gloves during the puncture procedure. It is therefore not practical to operate the apparatus during the puncture procedure.

In order to image the puncture needle 1a with highest brightness, it is necessary to apply an ultrasonic beam perpendicular to the puncture needle 1a. In the first embodiment, even when the puncture needle 1a is inserted at any angle, the transmission direction of an ultrasonic beam perpendicular to the puncture needle 1a can be directly found by detecting the line segment corresponding to the puncture needle 1a through image processing. In the first embodiment, therefore, the visibility of the puncture needle can be improved irrespective of the angle of the puncture needle.

In the first embodiment, the direction and/or the number of directions of ultrasound transmission performed in the second scan is changed based on the angle and/or the temporal change of the angle. Accordingly, even when the puncture angle fluctuates, it can be ensured that oblique image data in the direction close to the perpendicular to the puncture needle 1a is captured. In the first embodiment, the frame rate of composite image data can be kept because the scan line density is changed with the change of the number of transmission directions.

Second Embodiment

In a second embodiment, a modification of the processing by the image generation controller 183 that is performed after the scan control similar to the first scan and the second scan explained in the first embodiment will be described with reference to FIG. 7. FIG. 7 is a diagram illustrating an overview of an image generation control processing performed in the second embodiment.

The ultrasonic diagnosis apparatus according to the second embodiment is configured in the same manner as the ultrasonic diagnosis apparatus explained in the first embodiment described with reference to FIG. 1. The second embodiment, however, differs from the first embodiment in that the processing by the selector 183a is performed after the processing by the extractor 183b is performed. In the following, differences from the first embodiment will be mainly described. The matters mentioned in the first embodiment are applied to the matters not specifically mentioned in the following description.

In the second embodiment, the image generation controller 183 controls the image generator 14 to generate needle image data, based on the angle calculated by the detector 182 for each image data that constitutes the image data group based on the second ultrasonic image group.

Specifically, the extractor 183b according to the second embodiment controls the image generator 14 to generate a candidate image data group in which a high-brightness region is extracted, by performing a threshold processing on each image data that constitutes the second ultrasonic image data group. Specifically, the image generator 14 sets the brightness value of a pixel having a brightness value smaller than a threshold for high-brightness region extraction in the oblique image data, to "0", under the control of the extractor 183b. The image generator 14 thus generates candidate image data in which only pixels having a brightness value equal to or larger than the threshold for high-brightness region extraction are extracted with high brightness.

For example, the image generator 14 generates candidate data with "the oblique angle: α1" from ultrasonic image data with "the oblique angle: α1", generates candidate data with "the oblique angle: α2" from ultrasonic image data with "the oblique angle: α2", and generates candidate data with "the oblique angle: α3" from ultrasonic image data with "the oblique angle: α3" (see (1) in FIG. 7).

The detector 182 according to the second embodiment then calculates the angle (β) of the puncture needle by performing a line segment detection processing on each candidate image data (see (2) in FIG. 7).

The selector 183a according to the second embodiment then selects image data generated through ultrasound transmission performed in a direction suitable for visualizing the puncture needle 1a as needle image data from the candidate image data group, based on the angle calculated by the detector 182 (see (3) in FIG. 7). That is, the selector 183a selects candidate image data with the oblique angle closest to the angle (β) as needle image data.

The image combiner 16 then generates composite image data of the first ultrasonic image data and the needle image data through a combining processing (see (4) in FIG. 7). The display controller 184 then controls the composite image data to be displayed on the monitor 2. The combining processing performed in the second embodiment is performed in the same manner as the combining processing described in the first embodiment. The processing of changing the oblique angle and the number of oblique directions and the processing of changing ultrasound transmission/reception conditions as described in the first embodiment are also performed in the second embodiment.

Figure 8:
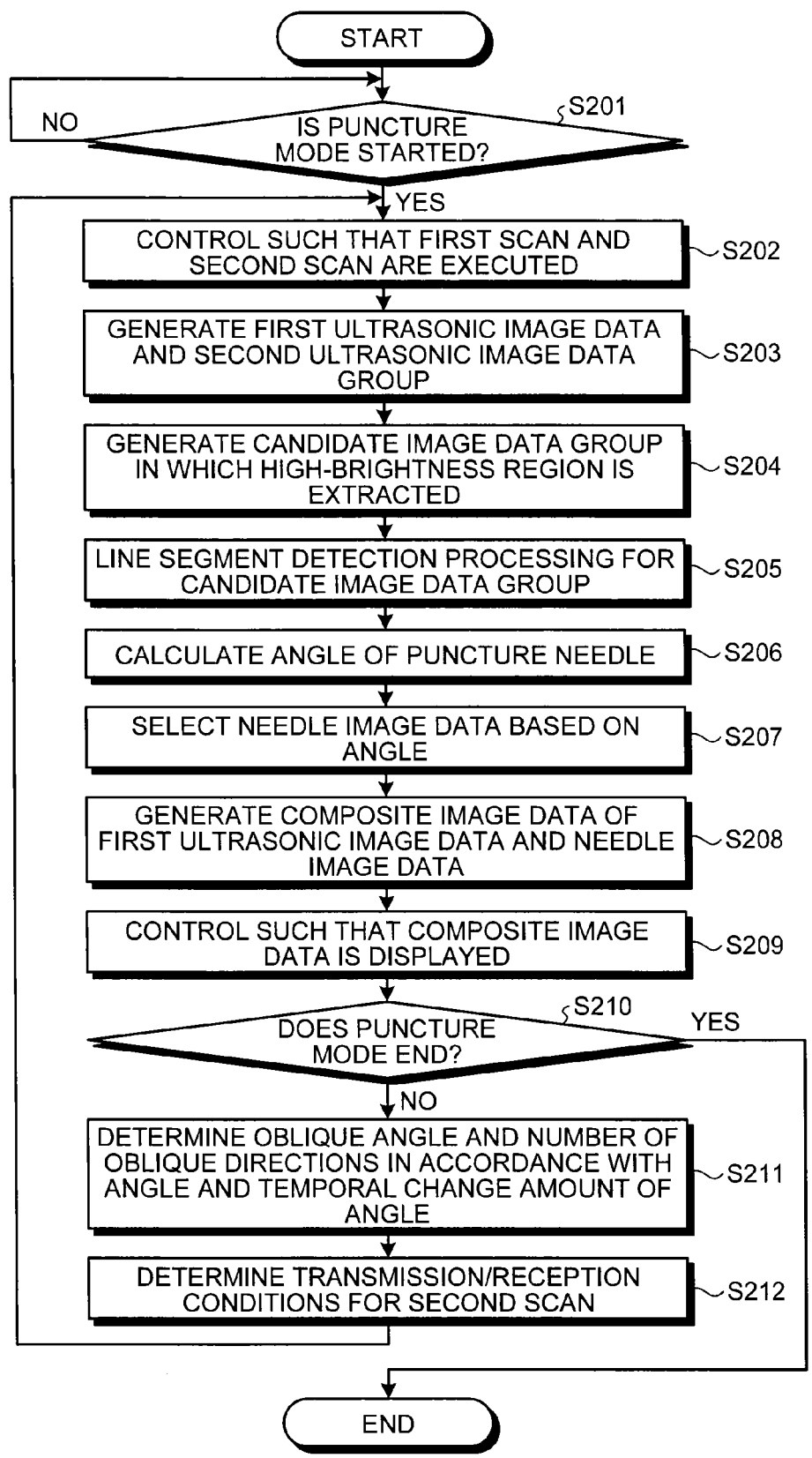
FIG. 8 is a flowchart for explaining an example of a processing by the ultrasonic diagnosis apparatus according to the second embodiment.

Next, an example of the processing by the ultrasonic diagnosis apparatus according to the second embodiment will be described with reference to FIG. 8. FIG. 8 is a flowchart for explaining an example of the processing by the ultrasonic diagnosis apparatus according to the second embodiment.

As illustrated in FIG. 8, the ultrasonic diagnosis apparatus according to the second embodiment determines whether the puncture mode is started (Step S201). Here, if the puncture mode is not started (No at Step S201), the ultrasonic diagnosis apparatus according to the second embodiment waits until the puncture mode is started.

On the other hand, if the puncture mode is started (Yes at Step S201), the scan controller 181 controls the ultrasound probe 1 such that the first scan and the second scan are executed (Step S202).

The image generator 14 then generates the first ultrasonic image data and the second ultrasonic image data group (Step S203). The image generator 14 then generates a candidate image data group in which a high-brightness region is extracted, from the second ultrasonic image data group, under the control of the extractor 183b (Step S204). The detector 182 then performs a line segment detection processing on the candidate image data group (Step S205) and calculates the angle of the line segment, that is, the angle of the puncture needle 1a (Step S206).

The selector 183a then selects needle image data from the candidate image data group, based on the angle (Step S207). The image combiner 16 then generates a composite image of the first ultrasonic image data and the needle image data (Step S208). The display controller 184 controls such that the composite image data is displayed (Step S209).

The scan controller 181 then determines whether the puncture mode ends (Step S210). Here, if the puncture mode does not end (No at Step S210), the scan controller 181 determines the oblique angle and the number of oblique directions in accordance with the angle and the temporal change amount of the angle (Step S211). The scan controller 181 then determines transmission/reception conditions for the second scan, based on the result of the decision processing performed at Step S211 (Step S212), and returns to Step S202 to control the ultrasonic diagnosis apparatus such that the first scan and the second scan for generating a composite image for the next frame are executed.

On the other hand, if the puncture mode ends (Yes at Step S210), the ultrasonic diagnosis apparatus terminates the processing. The display controller 184 may display the first ultrasonic image data, the second ultrasonic image group, or the candidate image data group concurrently with the composite image data. In the foregoing description, a case is explained where the puncture mode end determination is performed after display of the composite image at Step S209. In the second embodiment, however, the puncture mode end determination may be performed after the first scan and the second scan of Step S202 are performed. That is, the first scan and the second scan may be performed in a sequential order concurrently with the processing at Step S203 to Step S209.

As described above, in the second embodiment, a candidate image data group selectable as needle image data is generated by extracting a high-brightness region in each oblique image data in advance. In the second embodiment, the candidate image data corresponding to the oblique angle closest to the calculated angle is then selected as needle image data. This also makes it possible to improve the visibility of the puncture needle irrespective of the angle of the puncture needle.

In the second embodiment, the brightness value of each pixel that constitutes the first ultrasonic image data may be used as a threshold for high-brightness region extraction. In the second embodiment, image data obtained by subtracting the first ultrasonic image data from each image data that constitutes the second ultrasonic image data group may be used as the candidate image data.

Third Embodiment

Figure 9:
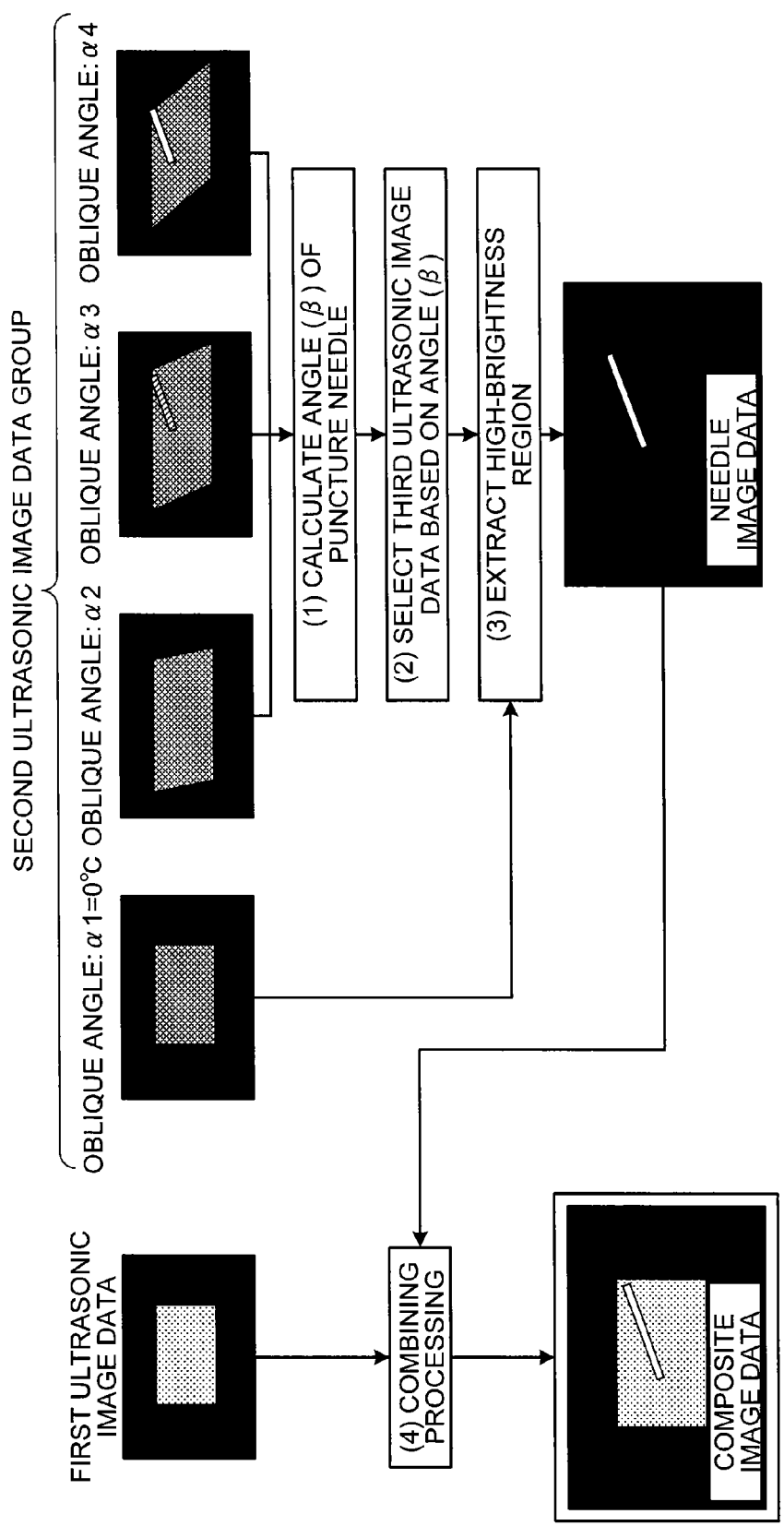
FIG. 9 is a diagram illustrating an overview of an image generation control processing performed in a third embodiment.

In a third embodiment, a case where the second scan different from the second scan described in the first and second embodiments will be described with reference to FIG. 9, etc. FIG. 9 is a diagram illustrating an overview of an image generation control processing performed in the third embodiment.

The ultrasonic diagnosis apparatus according to the third embodiment is configured in the same manner as the ultrasonic diagnosis apparatus described in the first embodiment described with reference to FIG. 1. The matters mentioned in the first embodiment, etc., are applied to the matters not specifically mentioned in the following description.

The scan controller 181 according to the third embodiment performs the first scan described in the first and second embodiments. The scan controller 181 according to the third embodiment causes the ultrasound probe 1 to perform ultrasound transmission in each of a plurality of directions including the direction perpendicular to the transducer element surface, as the second scan. That is, the second scan according to the third embodiment includes a scan with the oblique angle "0 degrees". The oblique angle "0 degrees" is usually a first direction performed in the first scan. For example, in a case of four directions as illustrated in FIG. 9, the oblique angles are "α1, α2, α3, α4", where al is 0 degrees. Accordingly, the image generator 14 generates ultrasonic image data with "the oblique angle: α1=0 degrees", ultrasonic image data with "the oblique angle: α2", ultrasonic image data with "the oblique angle: α3", and ultrasonic image data with "the oblique angle: α4" as the second ultrasonic image data group, as illustrated in FIG. 9.

In the third embodiment, the ultrasound transmission/reception conditions for the second scan are set such that artifacts due to grating lobes are minimized and the reception signal from the puncture needle 1a is larger, in the same manner as in the first embodiment. For example, the ultrasound transmission/reception conditions for the second scan are set such that a transmission waveform at a relatively low frequency is transmitted from the ultrasound probe 1, and a fundamental component of the transmitted ultrasonic wave is used in the processing of the received signal.

The detector 182 according to the third embodiment then performs a line segment detection processing and an angle detection processing on each image data generated through ultrasound transmission/reception performed from among the second ultrasonic image data group in a direction other than the perpendicular direction. For example, the detector 182 calculates the angle ($\beta$) for ultrasonic image data with "the oblique angle: α2", ultrasonic image data with "the oblique angle: α3", and ultrasonic image data with "the oblique angle: α4" (see (1) in FIG. 9).

The selector 183a according to the third embodiment selects the third ultrasonic image data from a plurality of oblique image data other than the "oblique angle: 0 degrees" from among the second ultrasonic image data group, based on the angle ($\beta$) calculated by the detector 182, as described in the first embodiment.

The extractor 183b according to the third embodiment then extracts a high-brightness region (puncture needle region), based on the third ultrasonic image data and the "oblique image data with the oblique angle of 0 degrees" (see (3) in FIG. 9). The extractor 183b then controls the image generator 14 to generate needle image data using the extracted puncture needle region.

In the first embodiment, a high-brightness region (puncture needle region) is extracted from the oblique image data selected as the third ultrasonic image data. In the first embodiment, however, a region in which a living tissue with high reflectivity is imaged may be extracted as a high-brightness region to become noise of the needle image data. Meanwhile, in the "oblique image data with the oblique angle of 0 degrees" generated under the same transmission/reception conditions as the third ultrasonic image data, although it is unlikely that a high-brightness region resulting from the puncture needle 1a is included, it is likely that a high-brightness region resulting from a living tissue with high reflectivity is included.

The extractor 183b according to the third embodiment performs an extraction processing described below so that no noise is included in a high-brightness region to be used to generate needle image data, by using the "oblique image data with the oblique angle of 0 degrees".

The extractor 183b compares the brightness value of the "oblique image data with the oblique angle of 0 degrees" with the third ultrasonic image data, pixel by pixel. The extractor 183b then sets a pixel of brightness value where "oblique image data with the oblique angle of 0 degrees" is larger, to "0". The extractor 183b sets a pixel of brightness value where the third ultrasonic image data is larger, as a pixel that constitutes a high-brightness region as it is. The extractor 183b then notifies the image generator 14 of the position of the pixel having the brightness value set to "0", among pixels that constitute the third ultrasonic image data. The image generator 14 thus generates needle image data in which a high-brightness region (puncture needle region) of the third ultrasonic image data is extracted, as illustrated in FIG. 9.

The extractor 183b may generate image data obtained by subtracting the brightness value of the "oblique image data with the oblique angle of 0 degrees" from the brightness value of the third ultrasonic image data, pixel by pixel, as needle image data. The extractor 183b may generate image data obtained by performing weighted addition/subtraction on the brightness value of the third ultrasonic image data and the brightness value of the "oblique image data with the oblique angle of 0 degrees" pixel by pixel, as needle image data.

The image combiner 16 then generates composite image data of the first ultrasonic image data and the needle image data through a combining processing (see (4) in FIG. 9). The display controller 184 then controls the composite image data to be displayed on the monitor 2. The combining processing performed in the third embodiment is performed in the same manner as the combining processing explained in the first embodiment.

In the case where a puncture needle region of the third ultrasonic image data is extracted by comparing the brightness value pixel by pixel, the extractor 183b preferably performs the processing of extracting a puncture needle region, using image data with a reduced brightness value of the third ultrasonic image data. For example, the extractor 183b sets the gain of the third ultrasonic image lower relative to the "oblique image with the oblique angle of 0 degrees". Accordingly, the brightness value of the pixel corresponding to a living tissue in the third ultrasonic image data is set to "0" for sure by comparison of brightness values, thereby leaving only the puncture needle with high brightness.

In the oblique scan in general settings, the ultrasonic diagnosis apparatus performs brightness adjustment by performing gain adjustment or dynamic range adjustment so that the overall brightness of each of the oblique image data is approximately equal. Then, when the brightness value of the third ultrasonic image data and the brightness value of the "oblique image data with the oblique angle of 0 degrees" are compared pixel by pixel, the gain of the third ultrasonic image is intentionally reduced, whereby the puncture needle region of the third ultrasonic image data can be accurately extracted.

The processing of changing the oblique angle and the number of oblique directions and the processing of changing ultrasound transmission/reception conditions as explained in the first embodiment are also performed in the third embodiment.

For example, let us consider a case where a plurality of oblique angles set in the second scan when one frame of composite image data is generated are "$\{\alpha1, \alpha2, \alpha3, \alpha4\}=\{0$ degrees, 10 degrees, 20 degrees, 30 degrees$\}$" and the angle calculated by the detector 182 is "$\beta=28$ degrees". In this case, the scan controller 181 changes a plurality of oblique angles set in the second scan performed for generating the next frame of composite image data to "$\{\alpha1, \alpha2, \alpha3, \alpha4\}=\{0$ degrees, 23 degrees, 28 degrees, 33 degrees$\}$".

As an another example, let us consider a case where a plurality of oblique angles set in the second scan when the "n-th" frame of composite image data is generated are "$\{\alpha1, \alpha2, \alpha3, \alpha4\}=\{0$ degrees, 10 degrees, 20 degrees, 30 degrees$\}$" and the angle calculated by the detector 182 is "$\beta=28$ degrees". It is further assumed that the temporal change ($d\beta/dt$) calculated between the angle obtained when the "(n−1)th" frame of composite image data is generated and the angle obtained when the "n-th" frame of composite image data is generated is "$d\alpha/dt \geq TH(\beta)$". In this case, the scan controller 181 changes a plurality of oblique angles set in the second scan to be performed for generating the "(n+1)th" frame of composite image data to "$\{\alpha1, \alpha2, \alpha3, \alpha4, \alpha5, \alpha6\}=\{0$ degrees, 18 degrees, 23 degrees, 28 degrees, 33 degrees, 38 degrees$\}$".

In this case, the scan controller 181 sets the density of transmission/reception beams for generating one frame of oblique image data to "4/6" of the present state because the number of oblique directions is changed from four directions to six directions. Accordingly, in the present embodiment, the frame rate of the composite image can be kept.

The processing performed by the ultrasonic diagnosis apparatus according to the third embodiment differs from the processing performed by the ultrasonic diagnosis apparatus according to the first embodiment described with reference to FIG. 6 in the following points. Namely, the third embodiment differs from the first embodiment in that the second scan includes the oblique angle "0 degrees" at Step S102 in FIG. 6. In addition, the third embodiment differs from the first embodiment in that the line segment detection processing at Step S104 in FIG. 6 is targeted for the second ultrasonic image data group other than the "oblique image with the oblique angle of 0 degrees". The processing performed by the ultrasonic diagnosis apparatus according to the third embodiment differs from the first embodiment in that the "oblique image with the oblique angle of 0 degrees" is used in the processing at Step S107 in FIG. 6.

As described above, in the third embodiment, brightness value comparison is performed between pixels using the "oblique image with the oblique angle of 0 degrees", thereby avoiding inclusion of noise components in a high-brightness region extracted from the third ultrasonic image data. Accordingly, in the third embodiment, the visibility of the puncture needle can be further improved.

In the third embodiment, a high-brightness region is extracted after the brightness value of the third ultrasonic image data is reduced, whereby the puncture needle region can be extracted for sure.

Fourth Embodiment

Figure 10:
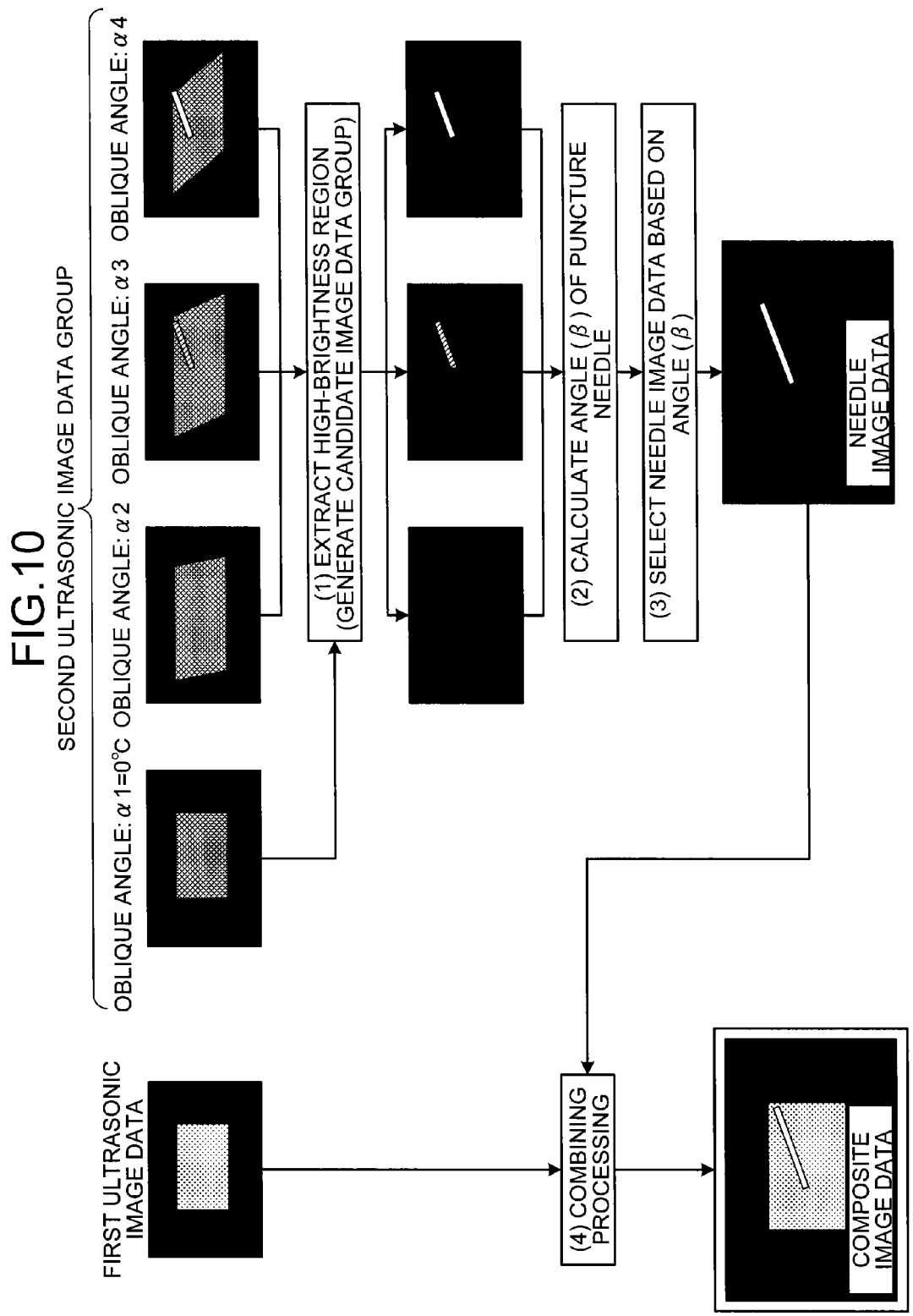
FIG. 10 is a diagram illustrating an overview of an image generation control processing performed in a fourth embodiment.

In a fourth embodiment, a modification of the processing by the image generation controller 183 that is performed after the same scan control as the first scan and the second scan explained in the third embodiment will be described with reference to FIG. 10. FIG. 10 is a diagram illustrating an overview of an image generation control processing performed in the fourth embodiment.

The ultrasonic diagnosis apparatus according to the fourth embodiment is configured in the same manner as the ultrasonic diagnosis apparatus described in the first embodiment described with reference to FIG. 1. The fourth embodiment, however, differs from the third embodiment in that the processing by the selector 183a is performed after the processing by the extractor 183b is performed. In the following, differences from the third embodiment will be mainly described. The matters mentioned in the first embodiment etc., are applied to the matters not specifically mentioned in the following description.

First, in the fourth embodiment, ultrasound transmission is also performed for each of a plurality of directions including the direction perpendicular to the transducer element surface, as the second scan, in the same manner as in the third embodiment. The image generator 14 thus generates, for example, ultrasonic image data with "the oblique angle: α1=0 degrees", ultrasonic image data with "the oblique angle: α2", ultrasonic image data with "the oblique angle: α3", and ultrasonic image data with "the oblique angle: α4" as the second ultrasonic image data group, as illustrated in FIG. 10.

In the fourth embodiment, the image generation controller 183 then controls the image generator 14 to generate needle image data, based on the angle calculated by the detector 182 for each image data that constitutes the image data group based on the second ultrasonic image data group.

Specifically, the extractor 183b according to the fourth embodiment controls the image generator 14 to generate an image data group obtained by subtracting image data generated through ultrasound transmission/reception performed as the second scan in the perpendicular direction from each image data generated through ultrasound transmission/reception performed in a direction other than the perpendicular direction from among the second ultrasonic image data group, as the candidate image data group.

Specifically, the image generator 14 generates a candidate image data group (subtraction image data group) in which a high-brightness region is extracted, by subtracting the brightness value of the "oblique image data with the oblique angle of 0 degrees" from the brightness value of the "oblique image data with the oblique angle other than the oblique angle of 0 degrees", pixel by pixel, under the control of the extractor 183b (see (1) in FIG. 10). The image generator 14 sets a pixel having a negative subtraction value to "0".

The "oblique image data with the oblique angle other than the oblique angle of 0 degrees" is image data in which the puncture needle 1a may be visualized well. The "oblique image data with the oblique angle of 0 degrees" is image data in which a living tissue is visualized well, under the ultrasound transmission/reception conditions for the second scan. Therefore, a plurality of image data that constitutes the candidate image data group generated through the subtraction processing above includes image data in which a high-brightness region corresponding to the puncture needle region is extracted. Such an image data group serves as an image data group including image data that can be selected as needle image data generated by comparing the brightness values pixel by pixel as described in the third embodiment.

In the fourth embodiment, therefore, any candidate image data of the candidate image data group is selected as needle image data. Based on this, in the fourth embodiment, it is preferable that the brightness value adjustment processing performed on the third ultrasonic image data in the third embodiment should be performed on the "oblique image data with the oblique angle other than the oblique angle of 0 degrees".

Specifically, the extractor 183b according to the fourth embodiment controls the image generator 14 to generate a candidate image data group using image data with a reduced brightness value of each image data generated through ultrasound transmission/reception performed in a direction other than the perpendicular direction from among the second ultrasonic image data group. Accordingly, inclusion of noise components in the high-brightness region of the candidate image data can be avoided for sure.

The detector 182 according to the fourth embodiment then calculates the angle (β) of the puncture needle by performing a line segment detection processing on each candidate image data (see (2) in FIG. 10).

The selector 183a according to the fourth embodiment then selects image data generated through ultrasound transmission performed in a direction suitable for visualizing the puncture needle 1a, as needle image data, from the candidate image data group, based on the angle calculated by the detector 182 (see (3) in FIG. 10). That is, the selector 183a selects candidate image data with the oblique angle closest to the angle (β) as needle image data.

The image combiner 16 then generates composite image data of the first ultrasonic image data and the needle image data through a combining processing (see (4) in FIG. 10). The display controller 184 then controls the composite image data to be displayed on the monitor 2. The combining processing performed in the fourth embodiment is performed in the same manner as the combining processing described in the first embodiment. In the fourth embodiment, the processing of changing the oblique angle and the number of oblique directions and the processing of changing ultrasound transmission/reception conditions as described in the third embodiment are also performed.

The processing performed by the ultrasonic diagnosis apparatus according to the fourth embodiment differs from the processing performed by the ultrasonic diagnosis apparatus according to the second embodiment described with reference to FIG. 8 in the following points. Namely, the fourth embodiment differs from the second embodiment in that the second scan includes the oblique angle of "0 degrees" at Step S202 in FIG. 8. In addition, the fourth embodiment differs from the second embodiment in that a candidate image data group is generated from "oblique image data with the oblique angle other than the oblique angle of 0 degrees" using the "oblique image data with the oblique angle of 0 degrees" in the processing at Step S204 in FIG. 8.

As described above, in the fourth embodiment, a candidate image data group that can be selected as needle image data is generated by extracting a high-brightness region in the "oblique image data with the oblique angle other than the oblique angle of 0 degrees" using the "oblique image data with the oblique angle of 0 degrees" in advance. In the fourth embodiment, the candidate image data corresponding to the oblique angle closest to the calculated angle is then selected as needle image data. This can also improve the visibility of the puncture needle irrespective of the angle of the puncture needle.

In the fourth embodiment, a high-brightness region is extracted using the "oblique image data with the oblique angle of 0 degrees" after the brightness value of the "oblique image data with the oblique angle other than the oblique angle of 0 degrees" is reduced, whereby the puncture needle region can be extracted for sure.

Fifth Embodiment

Figure 11:
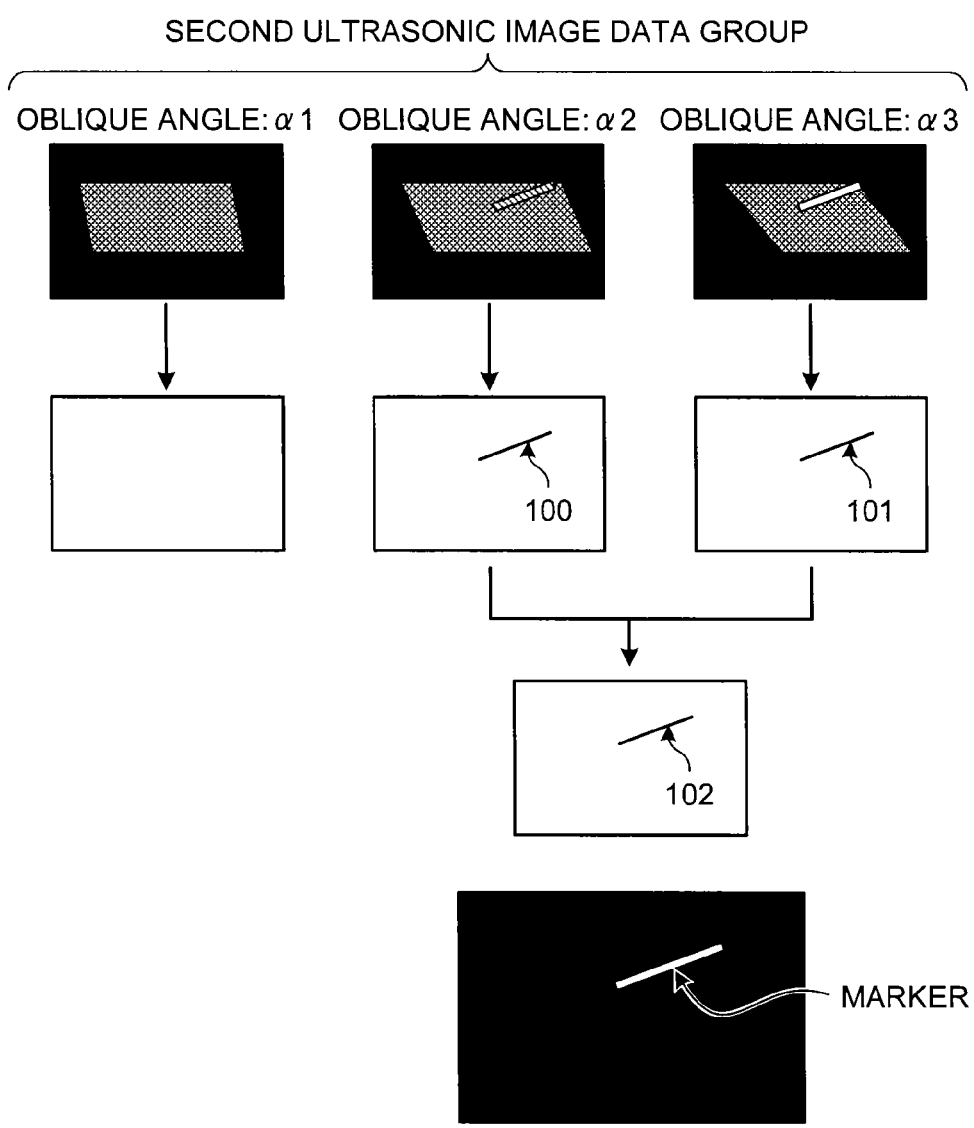
FIG. 11, FIG. 12 and FIG. 13 are diagrams for explaining a fifth embodiment.
Figure 12:
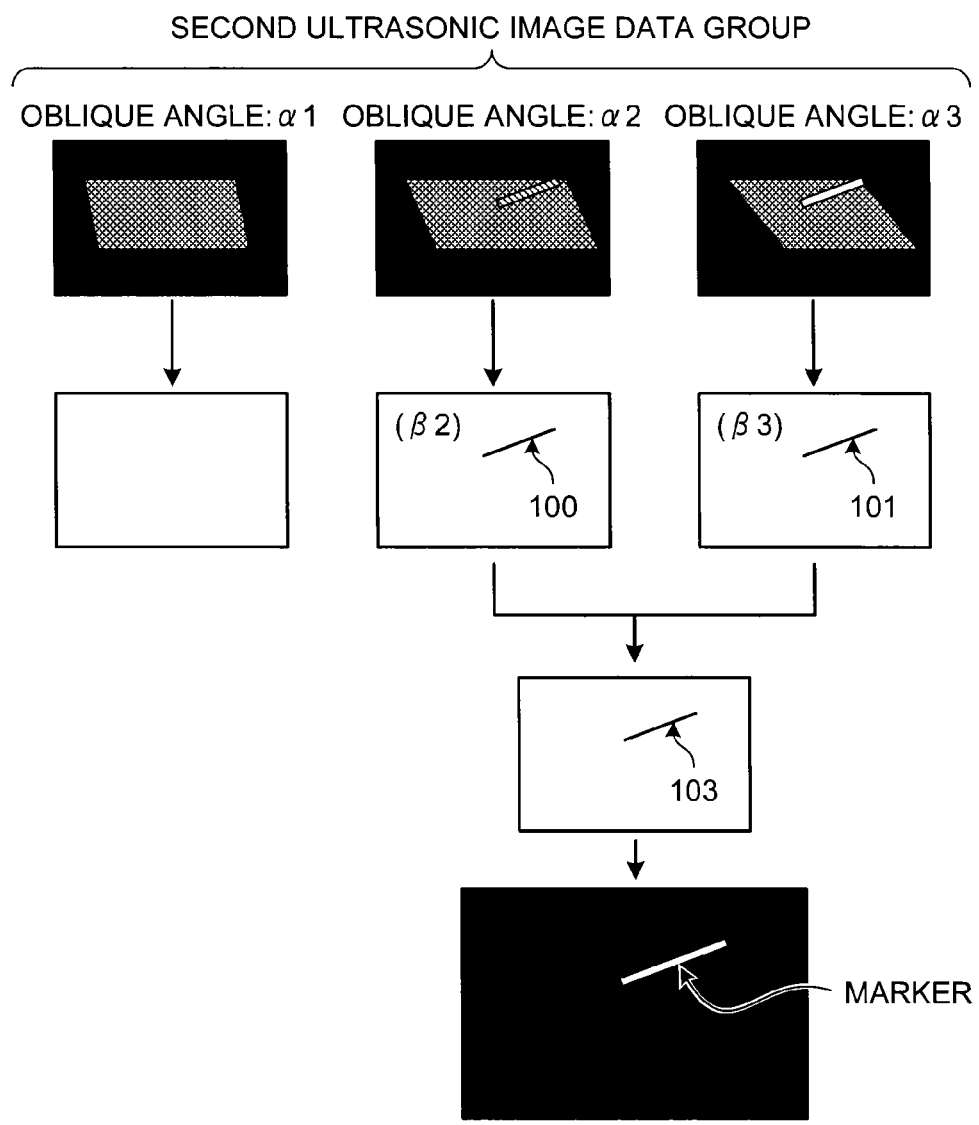
Figure 13:
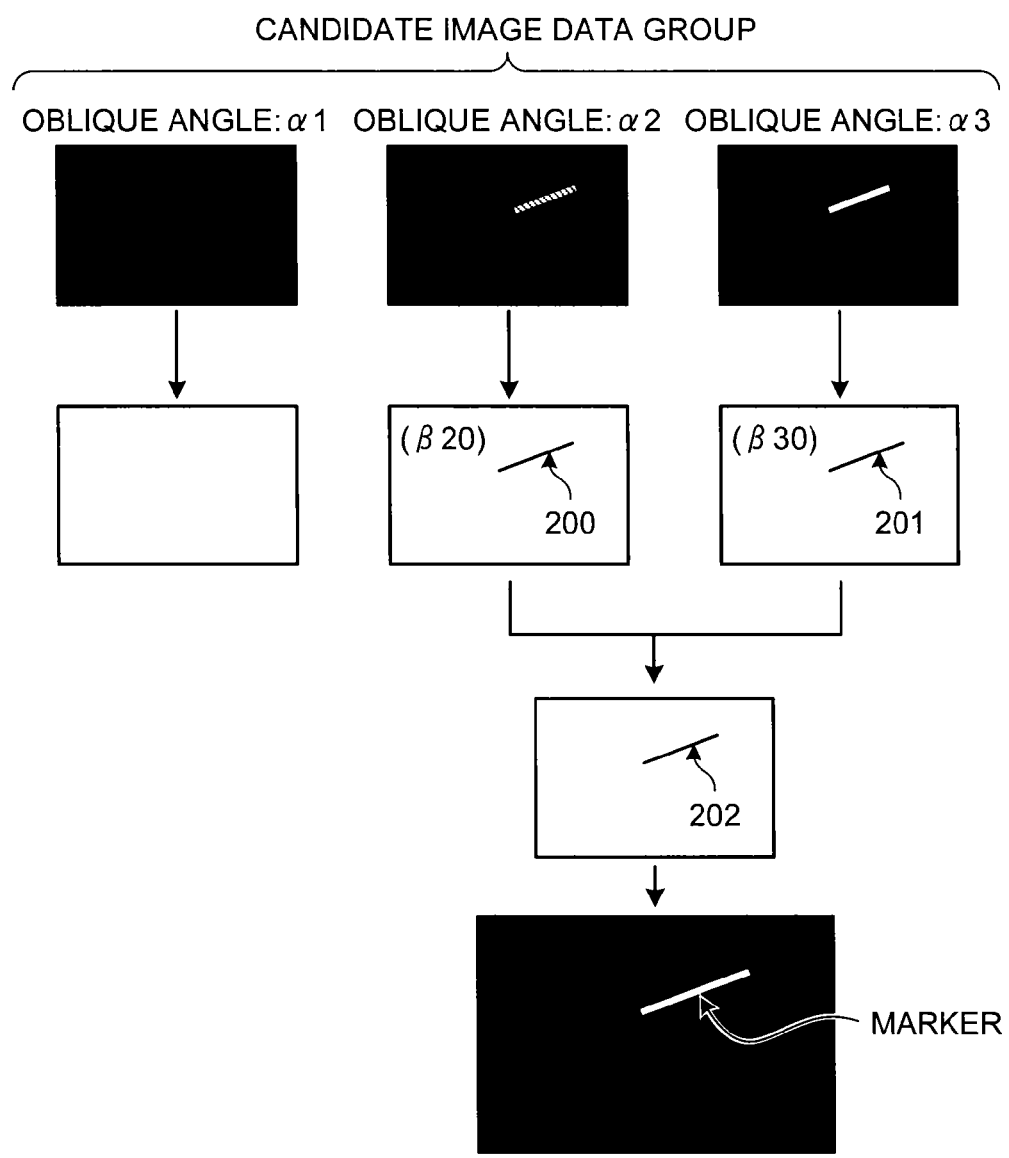

In a fifth embodiment, a modification of the foregoing first to fourth embodiments will be described with reference to FIGS. 11 to 13. FIGS. 11 to 13 are diagrams for explaining the fifth embodiment.

In the first to fourth embodiments, the case where needle image data is generated based on the angle calculated from the detected line segment has been described. The needle image data, however, may be generated based on the detected line segment.

In the first to fourth embodiments, the case where needle image data in which the puncture needle 1a is imaged is generated using ultrasonic image data has been described. Specifically, in the first and third embodiments, needle image data is generated using a region corresponding to the puncture needle 1a of the third ultrasonic image data. In the second and fourth embodiments, needle image data is selected from a candidate image data group. The needle image data, however, may be generated by drawing an artificial marker corresponding to the puncture needle 1a.

In the following, three modifications performed in the fifth embodiment will be described. In the first modification, the image generation controller 183 controls the image generator 14 to generate, as needle image data, image data in which a marker based on the line segment detected by the detector 182 for the second ultrasonic image data group is drawn. The second ultrasonic image data group illustrated in FIG. 11 is the same image data group as the second ultrasonic image data group illustrated in FIG. 3. The detector 182 determines that line segment detection is impossible for the ultrasonic image data with "the oblique angle: α1" as illustrated in FIG. 11. The detector 182 detects a line segment 100 from the ultrasonic image data with "the oblique angle: α2" as illustrated in FIG. 11. The detector 182 detects a line segment 101 from the ultrasonic image data with "the oblique angle: α3" as illustrated in FIG. 11.

Here, the image generation controller 183 selects a line segment for use to create a marker, using a threshold (hereinafter referred to as THL) for the length of a line segment. Let us consider a case where the length of the line segment 100 is equal to or larger than "THL" and the length of the line segment 101 is equal to or larger than "THL". In this case, the image generation controller 183 controls the image generator 14 to draw a marker based on the line segment 100 and the line segment 101. For example, the image generation controller 183 sets the average value of the length of the line segment 100 and the length of the line segment 101 as the length of the marker. For example, the image generation controller 183 compares the average brightness value of the region corresponding to the line segment 100 with the average brightness value of the region corresponding to the line segment 101 and decides to arrange a marker in the line segment with the higher value. In the case illustrated in FIG. 11, the image generation controller 183 decides to arrange a marker in the line segment 101.

Accordingly, as illustrated in FIG. 11, a line segment 102 based on the line segment 100 and the line segment 101 is determined. The image generator 14 then draws a marker at the position corresponding to the line segment 102, as illustrated in FIG. 11. The image generator 14 then outputs, to the image combiner 16, image data in which a marker is drawn as needle image data. Alternatively, the image generator 14 may output image data in which ultrasonic image data with "the oblique angle: α2", ultrasonic image data with "the oblique angle: α3", and the marker are superimposed on one another, as needle image data, to the image combiner 16. In this case, the image generator 14 uses addition image data, arithmetic mean image data, or weighted addition image data of the ultrasonic image data "with the oblique angle: α2" and the ultrasonic image data "with the oblique angle: α3", as a target to be superimposed with the marker. In the case where weighed addition is performed, the weight is determined, for example, based on the average brightness value of the region corresponding to the line segment.

If the length of the line segment 101 is equal to or larger than "THL" and the length of the line segment 100 is equal to or shorter than "THL", a marker based on the line segment 101 is drawn.

In the second modification, the image generation controller 183 controls the image generator 14 to generate, as needle image data, image data in which a marker based on the line segment and the angle obtained by the detector 182 for the second ultrasonic image data group is drawn. The second ultrasonic image data group illustrated in FIG. 12 is the same image data group as the second ultrasonic image data group illustrated in FIG. 11. The line segment 100 and the line segment 101 illustrated in FIG. 12 are the same as the line segment 100 and the line segment 101 illustrated in FIG. 11.

The detector 182 further calculates the angle "β2" of the line segment 100 and calculates the angle "β3" of the line segment 101 as illustrated in FIG. 12. Let us consider a case where the length of the line segment 100 is equal to or larger than "THL" and the length of the line segment 101 is equal to or larger than "THL". In this case, the image generation controller 183 controls the image generator 14 to draw a marker based on the line segment 100 and the line segment 101 and the angle "β2" and the angle "β3". For example, the image generation controller 183 sets the average value of the length of the line segment 100 and the length of the line segment 101 as the length of the marker. For example, the image generation controller 183 sets the average angle of the angle "β2" and the angle "β3" as the angle of the marker. The image generation controller 183 sets the end point of the depth in the marker, for example, as the end point of the depth in the line segment 101 with a high average brightness value.

Accordingly, as illustrated in FIG. 12, a line segment 103 based on the line segment 100 and the line segment 101 and the angle "β2" and the angle "β3" is determined. The image generator 14 then draws a marker at the position corresponding to the line segment 103 as illustrated in FIG. 11. The image generator 14 then outputs the image data in which the marker is drawn, as needle image data to the image combiner 16. Alternatively, the image generator 14 may output image data in which the ultrasonic image data with "the oblique angle: α2", the ultrasonic image data with "the oblique angle: α3", and the marker are superimposed on one another, as needle image data to the image combiner 16. When a superimposing processing is performed, the same processing as the processing described above is applied.

When angle calculation is performed, the processing may be performed only using the third ultrasonic image data. In this case, a marker based on the line segment 101 detected in the ultrasonic image data with "the oblique angle: α3" that is the third ultrasonic image data is drawn. The processing that is targeted for the second ultrasonic image data group as described with reference to FIGS. 11 and 12 can be applied even when the second scan described in the third embodiment is performed.

In the third modification, the image generation controller 183 controls the image generator 14 to generate, as needle image data, image data in which a marker based on the line segment and the angle acquired by the detector 182 for the candidate image data group described in the second or third embodiment is drawn. The candidate image data group illustrated in FIG. 13 is the same image data group as the candidate image data group illustrated in FIG. V.

The detector 182 determines that line segment detection is impossible for the candidate image data with "the oblique angle: α1", as illustrated in FIG. 13. The detector 182 detects a line segment 200 from the candidate image data with "the oblique angle: α2" as illustrated in FIG. 13. The detector 182 also detects a line segment 201 from the candidate image data with "the oblique angle: α3" as illustrated in FIG. 13.

The detector 182 then calculates the angle "β20" of the line segment 200 and calculates the angle "β30" of the line segment 201, as illustrated in FIG. 13. Let us consider a case where the length of the line segment 200 is equal to or larger than "THL" and the length of the line segment 201 is equal to or larger than "THL". In this case, the image generation controller 183 controls the image generator 14 to draw a marker based on the line segment 200 and the line segment 201 and the angle "β20" and the angle "β30". For example, the image generation controller 183 sets the average value of the length of the line segment 200 and the length of the line segment 201 as the length of the marker. For example, the image generation controller 183 sets the average angle of the angle "β20" and the angle "β30" as the angle of the marker. The image generation controller 183 sets the end point of the depth in the marker, for example, as the end point of the depth in the line segment 201 with the higher brightness value.

Accordingly, as illustrated in FIG. 13, a line segment 203 based on the line segment 200 and the line segment 201 and the angle "β20" and the angle "β30" is determined. The image generator 14 then draws a marker at the position corresponding to the line segment 203 as illustrated in FIG. 13. The image generator 14 then outputs the image data in which the marker is imaged as needle image data to the image combiner 16. Alternatively, the image generator 14 may output image data in which candidate image data with "the oblique angle: α2", candidate image data with "the oblique angle: α3", and the marker are superimposed on one another, as needle image data to the image combiner 16. When the superimposing processing is performed, the same processing as the processing as described above is applied.

The processing illustrated in FIG. 13 may be performed only using the candidate image data selected as needle image data in the second and fourth embodiments. In this case, for example, a marker based on the line segment 201 detected in the candidate image data with "the oblique angle: α3" selected as needle image data is drawn.

As described above, even when needle image data in which an artificial marker representing the puncture needle 1a is imaged is used, the visibility of the puncture needle can be improved irrespective of the angle of the puncture needle.

The components of each apparatus described in the first to fifth embodiments are functionally conceptual and not always physically configured as illustrated in the figures. That is, the specific manner of distribution and integration of each apparatus is not limited to the one illustrated in the figures, and each apparatus can be entirely or partially configured to be functionally or physically distributed or integrated in a desired unit, depending on various loads or use conditions. Each processing function performed in each apparatus may be entirely or partially implemented by a CPU and a program analyzed and executed in the CPU, or implemented as hardware with wired logics.

The image processing method explained in the first to fifth embodiments can be implemented by causing a computer such as a personal computer or a workstation to execute an image processing program prepared beforehand. The image processing program can be distributed over a network such as the Internet. The image processing program may be recorded on a computer-readable non-transitory recording medium such as a hard disk, a flexible disk (FD), a compact disc-read only memory (CD-ROM), a magnetic optical disk (MO), a digital versatile disk (DVD), or a Flash memory such as a universal serial bus (USB) memory and a secure digital (SD) card memory and be read out from the non-transitory recording medium by a computer for execution.

As described above, the first to fifth embodiments can improve the visibility of the puncture needle irrespective of the angle of the puncture needle.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnosis apparatus, comprising:
   a scan controller that causes an ultrasound probe to execute a first scan for performing ultrasound transmission in a first direction relative to a transducer element surface for the purpose of visualizing a tissue of a subject and a second scan for performing ultrasound transmission in each of a plurality of directions relative to the transducer element surface including a direction perpendicular to the transducer element surface, in ultrasound scanning of the subject into which a puncture needle is inserted;
   image generation circuitry that generates first ultrasonic image data using a reflected wave received by the ultrasound probe through the first scan and that generates a second ultrasonic image data group comprising ultrasonic image data for each of the plurality of the directions using a reflected wave received by the ultrasound probe through the second scan;
   a detector that detects a line segment-based on the second ultrasonic image data group and calculates an angle of the line segment for each image data that constitutes the second ultrasonic image data group and that is generated through ultrasound transmission/reception performed in a direction other than the perpendicular direction;

an image generation controller that (1) selects, from the second ultrasonic image data group, based on the angle, third ultrasonic image data generated through ultrasound transmission performed in a direction suitable for visualizing the puncture needle, (2) compares the third ultrasonic image data with oblique image data with an oblique angle of 0 degrees, the oblique image data being different from the first ultrasonic image data, (3) sets a brightness value of a pixel to be a reduced value where a brightness value of the oblique image data is larger than a brightness value of the third ultrasonic image data, thereby generating image data with reduced brightness, (4) extracts, based on the image data with the reduced brightness, a high-brightness region of the third ultrasonic image data as a puncture needle region, and (5) controls the image generation circuitry to generate needle image data in which the puncture needle is imaged, by using the extracted puncture needle region;

image combining circuitry that generates composite image data of the first ultrasonic image data and the needle image data; and a display controller that controls the composite image data to be displayed on a predetermined display.

2. The ultrasonic diagnosis apparatus according to claim 1, wherein
the image generation controller
(1) controls the image generation circuitry to generate a candidate image data group in which a high-brightness region is extracted, by performing a threshold processing on each image data that constitutes the second ultrasonic image data group, and
(2) selects image data generated through ultrasound transmission performed in a direction suitable for visualizing the puncture needle as the needle image data from the candidate image data group, based on the angle calculated by the detector for each image data that constitutes the candidate image data group.

3. The ultrasonic diagnosis apparatus according to claim 2, wherein
the image generation controller controls the image generation circuitry to generate an image data group obtained by subtracting image data generated through ultrasound transmission/reception performed as the second scan in the perpendicular direction from each image data generated through ultrasound transmission/reception performed in a direction other than the perpendicular direction from among the second ultrasonic image data group, as the candidate image data group.

4. The ultrasonic diagnosis apparatus according to claim 2, wherein the direction suitable for visualizing the puncture needle is a direction at an angle closest to perpendicularity relative to the puncture needle.

5. The ultrasonic diagnosis apparatus according to claim 2, wherein the image generation controller controls the image generation circuitry to generate, as the needle image data, image data in which a marker based on the line segment and the angle acquired by the detector for the candidate image data group is drawn.

6. The ultrasonic diagnosis apparatus according to claim 1, wherein the direction suitable for visualizing the puncture needle is a direction at an angle closest to perpendicularity relative to the puncture needle.

7. The ultrasonic diagnosis apparatus according to claim 1, wherein the scan controller changes a direction of ultrasound transmission to be performed in the second scan, based on the angle calculated by the detector.

8. The ultrasonic diagnosis apparatus according to claim 7, wherein the scan controller changes an ultrasound transmission/reception condition for the second scan after change, based on a condition change of the second scan.

9. The ultrasonic diagnosis apparatus according to claim 1, wherein the scan controller changes a number of directions of ultrasound transmission to be performed in the second scan, based on a temporal change of the angle calculated by the detector.

10. The ultrasonic diagnosis apparatus according to claim 9, wherein the scan controller changes an ultrasound transmission/reception condition for the second scan after change, based on a condition change of the second scan.

11. The ultrasonic diagnosis apparatus according to claim 1, wherein the image generation controller controls the image generation circuitry to generate, as the needle image data, image data in which a marker based on the line segment detected by the detector for the second ultrasonic image data group is drawn.

12. The ultrasonic diagnosis apparatus according to claim 1, wherein the image generation controller controls the image generation circuitry to generate, as the needle image data, image data in which a marker based on the line segment and the angle acquired by the detector for the second ultrasonic image data group is drawn.

13. An image processing method, including:
causing, by a scan controller, an ultrasound probe to execute a first scan for performing ultrasound transmission in a first direction relative to a transducer element surface for the purpose of visualizing a tissue of a subject and a second scan for performing ultrasound transmission in each of a plurality of directions relative to the transducer element surface including a direction perpendicular to the transducer element surface, in ultrasound scanning of the subject into which a puncture needle is inserted;

generating, by image generation circuitry, first ultrasonic image data using a reflected wave received by the ultrasound probe through the first scan and that generates a second ultrasonic image data group comprising ultrasonic image data for each of the plurality of the directions using a reflected wave received by the ultrasound probe through the second scan;

detecting, by a detector, a line segment based on the second ultrasonic image data group;

calculating, by the detector, based on the second ultrasonic image data group, an angle of the line segment for each image data that constitutes the second ultrasonic image data group and that is generated through ultrasound transmission/reception performed in a direction other than the perpendicular direction;

selecting, by an image generation controller, from the second ultrasonic image data group, based on the angle, third ultrasonic image data generated through ultrasound transmission performed in a direction suitable for visualizing the puncture needle;

comparing, by the image generation controller, the third ultrasonic image data with oblique image data with an oblique angle of 0 degrees, the oblique image data being different from the first ultrasonic image data;

setting, by the image generation controller, a brightness value of a pixel to be a reduced value where a brightness value of the oblique image data is larger than a brightness value of the third ultrasonic image data, thereby generating, by the image generation controller, image data with a reduced brightness;

extracting, by the image generation controller, based on the image data with the reduced brightness, a high-brightness region of the third ultrasonic image data as a puncture needle region;

controlling, by the image generation controller, the image generation circuitry to generate needle image data in which the puncture needle is imaged, by using the extracted puncture needle region;

generating, by image combining circuitry, composite image data of the first ultrasonic image data and the needle image data; and controlling, by a display controller, the composite image data to be displayed on a predetermined display.

* * * * *